US008420334B2

(12) United States Patent
D'Souza-Schorey et al.

(10) Patent No.: US 8,420,334 B2
(45) Date of Patent: Apr. 16, 2013

(54) METHOD FOR DETECTING INVASIVE MICROVESICLES DERIVED FROM TUMOR CELLS

(75) Inventors: Crislyn D'Souza-Schorey, Granger, IN (US); James W. Clancy, South Bend, IN (US); Vandhana Muralidharan-Chari, Granger, IN (US)

(73) Assignee: University of Notre Dame, Notre Dame, IN (US)

( * ) Notice: Subject to any disclaimer, the term of this patent is extended or adjusted under 35 U.S.C. 154(b) by 69 days.

(21) Appl. No.: 12/942,858

(22) Filed: Nov. 9, 2010

(65) Prior Publication Data

US 2012/0115160 A1 May 10, 2012

(51) Int. Cl.
*G01N 33/53* (2006.01)

(52) U.S. Cl.
USPC .......................................................... 435/7.2

(58) Field of Classification Search ........................ None
See application file for complete search history.

(56) References Cited

PUBLICATIONS

Taraboletti et al. (2002) Amer. J. Pathology 106: 673-680.*
Wencel-Drake (1993) Blood 82: 1197-1203.*
Bogatcheva et al., Phorbol esters increase MLC phosphorylation and actin remodeling in bovine lung endothelium without increased contraction, Am J Physiol Lung Cell Mol Physiol, Aug. 2003, vol. 285, pp. L415-L426.
Bowden et al., Co-localization of cortactin and phosphotyrosine identifies active invadopodia in human breast cancer cells, Experimental Cell Research, May 1, 2006, vol. 312, Issue 8, pp. 1240-1253.
Dolo et al., Matrix-degrading proteinases are shed in membrane vesicles by ovarian cancer cells in vivo and in vitro, Clinical & Experimental Metastasis, 1999, vol. 17, pp. 131-140.
Dolo et al., Selective Localization of Matrix Metalloproteinase 9, B1 Integrins, and Human Lymphocyte Antigen Class I Molecules on Membrane Vesicles Shed by 8701-BC Breast Carcinoma Cells, Cancer Research, Oct. 1, 1998, vol. 58, pp. 4468-4474.
Donaldson, J., Multiple Roles for Arf6: Sorting, Structuring, and Signaling at the Plasma Membrane, The Journal of Biological Chemistry, Oct. 24, 2003, vol. 278, Issue 43, pp. 41573-41576.
D'Souza-Schorey et al., ARF proteins: roles in membrane traffic and beyond, Nature Reviews| Molecular Cell Biology, May 2006, vol. 7, pp. 347-358.
Fevrier et al., Exosomes: endosomal-derived vesicles shipping extracellular messages, Current Opinion in Cell Biology, Aug. 2004, vol. 16, Issue 4, pp. 415-421.
Goldberg et al., p38 MAPK activation by TGF-B1 increases MLC phosphorylation and endothelial monolayer permeability, Am J Physiol Lung Cell Mol Physiol, Jan. 2002, vol. 282, pp. L146-L154.
Graves et al., Proinvasive Properties of Ovarian Cancer Ascites-Derived Membrane Vesicles, Cancer Research, Oct. 1, 2004, vol. 64, pp. 7045-7049.
Hashimoto et al., Requirement for Arf6 in breast cancer invasive activities, PNAS, Apr. 27, 2004, vol. 101, Issue 17, pp. 6647-6652.

Heijnen et al., Activated Platelets Release Two Types of Membrane Vesicles: Microvesicles by Surface Shedding and Exosomes Derived From Exocytosis of Multivesicular Bodies and a-Granules, Blood, Dec. 1, 1999, vol. 94, Issue 11, pp. 3791-3799.
Hoover et al., Investigating the Role of ADP-Ribosylation Factor 6 in Tumor Cell Invasion and Extracellular Signal-Regulated Kinase Activation, Methods in Enzymology, 2005, vol. 404, pp. 134-147.
Hu et al., ADP-Ribosylation Factor 6 Regulates Glioma Cell Invasion through the IQ-Domain GTPase-Activating Protein 1-Rac1-Mediated Pathway, Cancer Res, Feb. 1, 2009, vol. 69, Issue 3, pp. 794-801.
Hugel et al., Membrane Microparticles: Two Sides of the Coin, Physiology, 2005, vol. 20, pp. 22-27.
Jovanovic et al., An Effector Domain Mutant of Arf6 Implicates Phospholipase D in Endosomal Membrane Recycling, Molecular Biology of the Cell, Jan. 2006, vol. 17, pp. 327-335.
Klemke et al., Regulation of Cell Motility by Mitogen-activated Protein Kinase, The Journal of Cell Biology, Apr. 21, 1997, vol. 137, Issue 2, pp. 481-492.
Manicourt et al., An Assay for Matrix Metalloproteinases and Other Proteases Acting on Proteoglycan, Casein, or Gelatin, Analytical Biochemistry, 1993, vol. 215, pp. 171-179.
Martínez-Lorenzo et al., Activated Human T Cells Release Bioactive Fas Ligand and APO2 Ligand in Microvesicles, J Immunol, 1999, vol. 163, pp. 1274-1281.
Morishige et al., GEP100 links epidermal growth factor receptor signaling to Arf6 activation to induce breast cancer invasion, Nature Cell Biology, Jan. 2008, vol. 10, Issue 1, pp. 85-102.
Muralidharan-Chari et al., ADP-Ribosylation Factor 6 Regulates Tumorigenic and Invasive Properties in vivo, Cancer Research, 2009, vol. 69, pp. 2201-2209.
Muralidharan-Chari et al., ARF6-regulated shedding of tumor-cell derived plasma membrane microvesicles, Curr Biol., Dec. 1, 2009, vol. 19, Issue 22, pp. 1875-1885.
Muralidharan-Chari et al., Microvesicles: mediators of extracellular communication during cancer progression, Journal of Cell Science, 2010, vol. 123, pp. 1603-1611.
Nekhoroshkova et al., A-RAF Kinase Functions in ARF6 Regulated Endocytic Membrane Traffic, PLoS ONE, Feb. 2009, vol. 4, Issue 2, pp. 1-18.
Nguyen et al., Myosin Light Chain Kinase Functions Downstream of Ras/ERK to Promote Migration of Urokinase-type Plasminogen Activator-stimulated Cells in an Integrin-selective Manner, The Journal of Cell Biology, Jul. 12, 1999, vol. 146, pp. 149-164.
Raposo et al., B Lymphocytes Secrete Antigen-presenting Vesicles, J. Exp. Med., Mar. 1996, vol. 183, pp. 1161-1172.
Robertson et al., Extracellular Signal-regulated Kinase Regulates Clathrin-independent Endosomal Trafficking, Molecular Biology of the Cell, Feb. 2006, vol. 17, pp. 645-657.

(Continued)

*Primary Examiner* — Michael Pak
(74) *Attorney, Agent, or Firm* — Knobbe Martens Olson & Bear LLP

(57) ABSTRACT

The present application relates to the isolation and analysis of populations of microvesicles, such as populations of microvesicles that are shed by tumor cells and contain the protein ARF6. Invasive microvesicles from tumor cells contain a variety of specific proteins, including ARF6.

17 Claims, 27 Drawing Sheets

PUBLICATIONS

Sobieszek et al., Ca2+—calmodulin-dependent modification of smooth-muscle myosin light-chain kinase leading to its co-operative activation by calmodulin, Biochem J., 1993, vol. 295, pp. 405-411.

Tague et al., ADP-ribosylation factor 6 regulates tumor cell invasion through the activation of the MEK-ERK signaling pathway, PNAS, Jun. 29, 2004, vol. 101, Issue 26, pp. 9671-9676.

Taraboletti et al., Bioavailability of VEGF in Tumor-Shed Vesicles Depends on Vesicle Burst Induced by Acidic pH1, Neoplasia, Feb. 2006, vol. 8, Issue 2, pp. 96-103.

Tushir et al., ARF6-dependent activation of ERK and Rac1 modulates epithelial tubule development, The EMBO Journal, 2007, vol. 26, pp. 1806-1819.

* cited by examiner

METHOD FOR DETECTING INVASIVE MICROVESICLES DERIVED FROM TUMOR CELLS

STATEMENT REGARDING FEDERALLY SPONSORED R&D

This invention was made with government support under Grant No. 5R56CA115316-02 awarded by the National Cancer Institute. The government has certain rights in this invention.

BACKGROUND OF THE INVENTION

1. Field of the Invention

The present application relates generally to microvesicles and their isolation and analysis, including methods of identifying populations of invasive microvesicles that contain the protein ARF6. As described in the examples below, invasive microvesicles from tumor cells contain a variety of specific proteins, including ARF6.

2. Description of the Related Art

Microvesicles are small, membrane-enclosed structures that are shed from a variety of cell types and can contain a variety of bioactive molecules, including nucleic acids and proteins. Microvesicle shedding by the outward fission of membrane vesicles from the cell surface is a selective process that occurs more frequently in certain cells, such as cancerous tumor cells. These released microvesicles (also referred to as microparticles, particles, and ectosomes) have been widely detected in various biological fluids, including peripheral blood, urine, saliva, and ascites.

Microvesicles are believed to facilitate various processes, including tumor invasion and metastasis, and are also believed to play a role in inflammation, coagulation, stem-cell renewal and expansion, evasion of the immune response, and bone mineralization. The composition of microvesicles, and thus their function, varies depending on the cells from which they originate. For example, microvesicles secreted by skeletal cells have been found to play a role in initiating bone mineralization, while microvesicles secreted from endothelial cells have been implicated in angiogenesis. Microvesicles are thought to play a role in metastasis by facilitating angiogenesis, escape from immune surveillance, and extra-cellular matrix (ECM) degradation. Proteolytic activity associated with microvesicles shed by tumor cells has been found to correlate with disease stage.

The process of metastasis occurs when cells detach from a primary tumor and invade surrounding tissues to reach other, distal locations. This process leads to the formation of secondary tumors, and is one of the life-threatening hallmarks of malignant cancer. Standardized screening methods and techniques that are sensitive enough to detect early-stage cancer and other diseases are currently unavailable for a variety of conditions, including ovarian, prostate, breast, glioma, and melanoma cancers. As a result, metastasis often occurs before a patient can be diagnosed and treated.

Recent studies show that a variety of molecules are involved with the complex process of metastasis. One such molecule is the protein known as ARF6, of the ARF family of small GTP-binding proteins, which regulates membrane trafficking and actin cytoskeleton remodeling and has a role in acquisition of migratory and invasive potential of cancer and other cell types. Recent studies utilizing in vitro cell invasion assays have indicated that in invasive melanoma, glioma, and breast cancer cell lines, the ARF6 GTP/GDP cycle can regulate the invasive potential of the cells. In addition, cellular depletion of ARF6 by siRNA or inhibition of ARF6 activation by expression of a dominant negative ARF6 mutant attenuates tumor cell invasion in vitro. Recent animal studies have also revealed a role for ARF6 activation in melanoma and glioma cell invasion (V. Muralidharan-Chari et al., *Cancer Res.* 69, 2201-09 (2009), B. Hu et al., *Cancer Res.* 69, 794-801 (2009)). Moreover, screening of various breast tumor cell lines reveals a direct correlation between ARF6 protein expression and invasive capacity (S. Hashimoto et al., *Proc. Natl. Acad. Sci.* 101, 6647-52 (2004)). In addition, a molecule known as ARF6 exchange factor GEP 100 is expressed in 70% of primary breast ductal carcinomas, and is preferentially co-expressed with EGFR in malignant tumors (M. Morishige et al., *Nat. Cell Biol.* 10, 85-92 (2008)).

SUMMARY OF THE INVENTION

The present application relates to the isolation, identification and analysis of populations of microvesicles, such as invasive microvesicles that are shed by tumor cells. As described in the examples below, invasive microvesicles from tumor cells contain a variety of specific proteins, including ARF6. Thus, in some embodiments the isolated microvesicles comprise the protein ARF6.

In some embodiments, invasive microvesicles are identified in a sample by centrifuging the sample to collect a population of microvesicles and assaying the prepared population of microvesicles for the protein ARF6, wherein detecting the protein ARF6 identifies the population of microvesicles as invasive microvesicles. Identification of invasive microvesicles can be used, for example, to assess the invasiveness of a tumor in a patient.

In other embodiments, invasive microvesicles are identified in a sample by preparing a population of microvesicles from the sample and assaying the prepared population of microvesicles for the presence of one or more proteins selected from the group consisting of ARF6, Vamp3, MHC class I, MT1-MMP, β1-integrin and β1-integrin receptor.

In some embodiments, the sample is a biological fluid. In some embodiments, the biological fluid is blood, serum, plasma, urine, saliva, or ascites. In some embodiments, the biological fluid is obtained by washing an anatomical structure of a subject, and then collecting the wash fluid after it has come in contact with the anatomical structure.

In some embodiments, the microvesicles are lysed prior to analysis. In other embodiments, the microvesicles are not lysed, and are analyzed whole. In some embodiments, the microvesicles are analyzed by contacting them with an antibody that binds to a protein being detected.

DETAILED DESCRIPTION OF THE PREFERRED EMBODIMENT

Figure 1A:
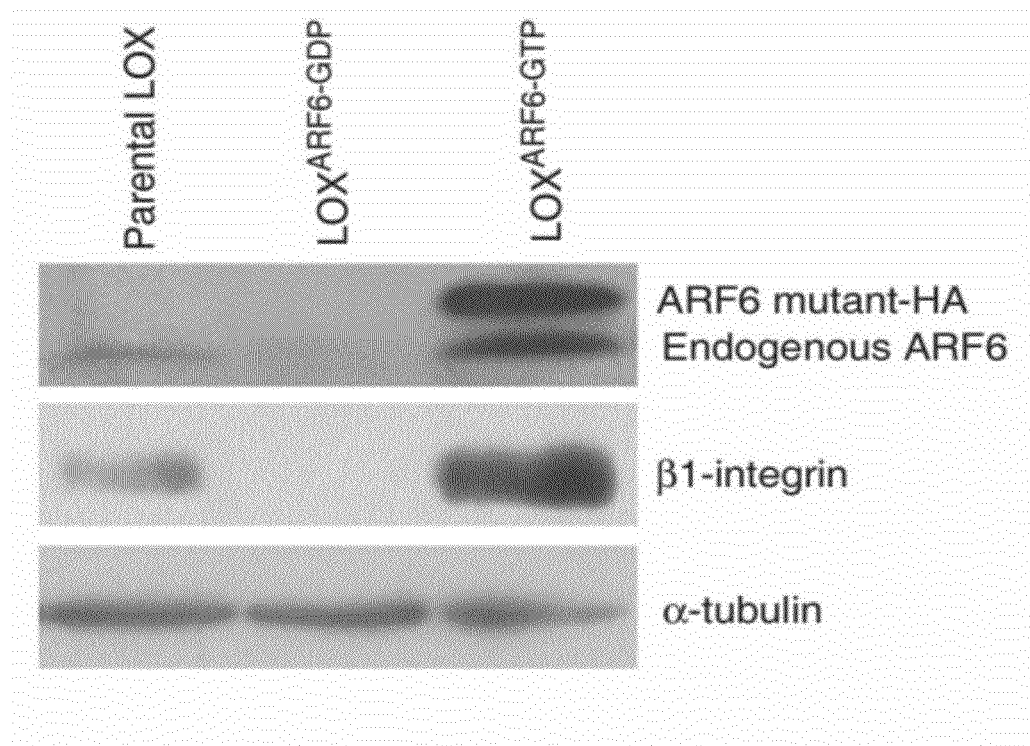
FIG. 1A shows vesicles released into the growth media from $2.2 \times 10^6$ LOX, LOXARF6-GTP, and LOXARF6-GDP cells, isolated and probed for ARF6 and β1 integrin by western blotting.

ARF6 has been suggested to play a role in tumor cell invasion and metastasis. ARF6 may promote cell invasion in a variety of ways, including through regulation of protease secretion. As discussed herein, via its effects on phospholipid metabolism and ERK activation, ARF6 regulates protease release by modulating the shedding of plasma membrane-derived microvesicles into the surrounding environment. Structural and biochemical characterization of ARF6-positive microvesicles shed by tumor cells shows that the protease cargo contained within the microvesicles is functionally robust and promotes extracellular matrix degradation. ARF6 also maneuvers the actomyosin machinery of cells to facilitate shedding of microvesicles from the tumor cell surface into the environment surrounding the cells. These findings are significant, particularly in light of reports demonstrating that proteolytic activities of microvesicles shed by tumor cells correlate directly with malignancy and invasiveness in cancer and other diseases (V. Dolo et al., *Clin. Exp. Metastasis* 17, 131-40 (1999), L. E. Graves et al., *Cancer Res.* 64, 7045-49 (2004)).

As described in the examples below, invasive microvesicles from tumor cells contain one or more specific proteins. In some embodiments, invasive microvesicles comprise ARF6. Other proteins present in invasive microvesicles may include one or more of Vamp3, MHC class I, MT1-MMP, β1-integrin and β1-integrin receptor. These proteins can be used to identify invasive microvesicles in a biological sample, such as a sample of biological fluid taken from a patient suffering from or suspected of suffering from a tumortdentification of a population of invasive microvesicles in a sample from a patient can be used, for example, to identify the presence of an invasive tumor in the patient and to assess the invasiveness of a known tumor.

Collection and Preparation of Microvesicles

A sample from a subject can be analyzed for the presence of microvesicles and, in particular, for the presence of invasive microvesicles. In some embodiments, the subject is a mammal. In other embodiments, the subject is a human. In some embodiments, the sample is a biological fluid from the subject. In some embodiments, the sample may be taken from a patient suffering from or suspected of suffering from a tumor. In other embodiments, the sample may be taken from a subject believed to be healthy. In some embodiments, a biological sample is taken from a subject suffering from a tumor, and the sample is taken from a region close to or associated with the tumor. In other embodiments, a biological sample is taken from a region located away from or unrelated to the tumor.

As microvesicles have been previously identified in blood, serum, plasma, urine, saliva and ascites, in some embodiments samples of one or more of these fluids are taken from a patient. Samples can be obtained using any of a variety of standard techniques. For example, blood or ascites can be removed from a patient with a needle and syringe, or any suitable suction device. In some embodiments the biological sample is not a fluid produced by the subject, but rather a fluid brought into contact with the subject. For example, a sample may be obtained by washing an anatomical structure and subsequently collecting the fluid that passed over the structure. This technique is often used during surgical procedures to collect samples of cells that may be present in various regions of a patient's body, such as the abdominal cavity. Further, a sample may be obtained by swabbing an anatomical structure, such as the inside of a patient's cheek. A sample may be subject to further processing, such as separating plasma from whole blood, prior to analyzing the sample for the presence of microvesicles and in particular for the presence of invasive microvesicles.

Once a sample is obtained it is centrifuged to separate the microvesicles, if present, from other components. The speed, duration, and temperature of centrifugation can be varied in order to obtain the desired results. In some embodiments, a sample is washed and centrifuged at about 5,000 g to 15,000 g at least once, preferably two or more times. In some embodiments the sample is centrifuged for about 10 to about 60 minutes, for example for about 10 minutes, 15 minutes, 20 minutes, or 25 minutes. In other embodiments, a sample is centrifuged for 35 minutes, 40 minutes, or 45 minutes. In a particular embodiment, a sample is centrifuged at about 10,000 g for about 30 minutes. In some embodiments, the sample is not centrifuged at a speed higher than about 30,000 g.

In other embodiments, a sample is first centrifuged at a lower speed, for example about 2,500 g prior to the higher speed centrifugation at about 5,000 g to 15,000 g as described above. In some embodiments, a sample is first centrifuged at about 1,200 g to about 3,000 g prior to the higher speed centrifugation. In some embodiments this first centrifugation removes cell nuclei, debris, and larger particulate matter from the sample. In some embodiments, a sample is first centrifuged at about 2,500 g for about 5 to about 30 minutes, followed by centrifugation at about 10,000 g as described above. Thus, in one embodiment the sample is centrifuged at about 2,500 g for 15 minutes, followed by centrifugation at 10,000 g for 30 minutes.

In some embodiments, the centrifugation steps are typically conducted at a temperature of less than about 10° C., such as about 2-10° C. However, in some other embodiments, the centrifugation steps are conducted at a temperature of about 8-18° C.

After centrifugation, the isolated microvesicles can be prepared for analysis. In some embodiments, the microvesicles are washed in phosphate buffered saline or another suitable solution. After washing, the microvesicles can be lysed using any of a variety of appropriate lysis buffers, such as RIPA buffer, that are well known to those of skill in the art. In some embodiments, the microvesicles are not lysed, but are analyzed whole.

Analysis of Microvesicle Contents

After collection of the microvesicles as described above, any of a variety of experimental techniques can be used to analyze them for the presence of one or more proteins selected from the group consisting of ARF6, Vamp3, MHC class I, MT1-MMP, β1-integrin and β1-integrin receptor. The presence of the assayed proteins indicates that the sample comprises invasive microvesicles.

In some embodiments, the microvesicles are assayed to determine if ARF6 is present. The presence of ARF6 and, typically, one or more additional proteins identifies the microvesicle population as comprising invasive microvesicles.

In some embodiments, microvesicles are assayed for the presence of ARF6 and one or more additional proteins selected from Vamp3, MHC class I, MT1-MMP, β1-integrin and β1-integrin receptor. In some embodiments invasive microvesicle populations are identified based on the presence of ARF6 and MT1-MMP.

In other embodiments, the presence of VAMP3, either alone or in combination with one or more additional proteins selected from ARF6, MHC class I, MT1-MMP, β1-integrin and β1-integrin receptor, is used to identify a population of microvesicles as comprising invasive microvesicles.

The microvesicles can be assayed for the presence of other combinations of proteins selected from selected from ARF6, Vamp3, WIC class I, MT1-MMP, β1-integrin and β1-integrin receptor. For example, they can be assayed for the presence of ARF6 and any combination of one or more of Vamp3, WIC class I, MT1-MMP, β1-integrin and β1-integrin receptor. Some exemplary combinations directed to ARF6 and one or more additional proteins are described below. Similar combinations can be assayed for substituting Vamp3 for ARF6. In all cases, the presence of the combination of proteins is indicative of a population of invasive microvesicles.

In some embodiments, the microvesicles are assayed for ARF6 as well as Vamp3 protein. In other embodiments, the microvesicles are assayed for ARF6 as well as WIC class I protein. In some embodiments, the microvesicles are assayed for ARF6 as well as β1 integrin. In other embodiments, the microvesicles are assayed for ARF6 as well as β1 integrin receptor. In other embodiments, the microvesicles are assayed for ARF6 as well as MT1-MMP.

In some embodiments, the microvesicles are assayed for ARF6, Vamp3, and WIC class I protein. In other embodiments, the microvesicles are assayed for ARF6, Vamp3, and β1 integrin. In other embodiments, the microvesicles are assayed for ARF6, Vamp3, and β1 integrin receptor. In other embodiments, the microvesicles are assayed for ARF6, Vamp3, β1 integrin and MT1-MMP. In other embodiments, the microvesicles are assayed for ARF6, Vamp3, β1 integrin receptor and MT1-MMP. In other embodiments, the microvesicles are assayed for ARF6, Vamp3, and MT1-MMP. In other embodiments, the microvesicles are assayed for ARF6, Vamp3, WIC class 1 and MT1-MMP. In other embodiments, the microvesicles are assayed for ARF6, Vamp3, WIC class I, and β1 integrin. In other embodiments, the microvesicles are assayed for ARF6, Vamp3, WIC class I, and β1 integrin receptor. In other embodiments, the microvesicles are assayed for ARF6, Vamp3, β1 integrin, and β1 integrin receptor. In other embodiments, the microvesicles are assayed for ARF6, Vamp3, WIC class I, β1 integrin and MT1-MMP. In other embodiments, the microvesicles are assayed for ARF6, Vamp3, WIC class I, β1 integrin receptor and MT1-MMP. In other embodiments, the microvesicles are assayed for ARF6, Vamp3, β1 integrin, β1 integrin receptor and MT1-MMP.

In other embodiments, the microvesicles are assayed for ARF6, MHC class I, β1 integrin, and β1 integrin receptor. In other embodiments, the microvesicles are assayed for ARF6, MHC class I, β1 integrin, β1 integrin receptor and MT1-MMP. In some embodiments, the microvesicles are assayed for ARF6, MHC class I, and β1 integrin. In some embodiments, the microvesicles are assayed for ARF6, MHC class I, and β1 integrin receptor. In some embodiments, the microvesicles are assayed for ARF6, MHC class I, β1 integrin and MT1-MMP. In some embodiments, the microvesicles are assayed for ARF6, MHC class I, β1 integrin receptor and MT1-MMP. In some embodiments, the microvesicles are assayed for ARF6, MHC class I, and MT1-MMP. In some embodiments, the microvesicles are assayed for ARF6, β1 integrin, and β1 integrin receptor. In some embodiments, the microvesicles are assayed for ARF6, β1 integrin, β1 integrin receptor and MT1-MMP. In some embodiments, the microvesicles are assayed for ARF6, Vamp3, MHC class I, β1 integrin, and β1 integrin receptor. In some embodiments, the microvesicles are assayed for ARF6, Vamp3, MHC class I, β1 integrin, β1 integrin receptor and MT1-MMP. In some embodiments, the microvesicles are assayed for ARF6, β1 integrin, and MT1-MMP. In some embodiments, the microvesicles are assayed for ARF6, β1 integrin receptor and MT1-MMP.

In some embodiments, the microvesicles are assayed for the presence of one or more of the proteins of interest, such as ARF6, Vamp3, MHC class I, MT1-MMP, β1-integrin and β1-integrin receptor, by contacting them with an antibody that specifically binds to the target protein that is being assayed. Antibodies to the target proteins are known in the art and are available from various sources. For example, anti-neutralizing β1-integrin, AIIB2, is available from the Developmental Studies Hybridoma Bank at the University of Iowa, anti-MHC-class I is available from Serotec, anti-MT1-MMP is available from Dr. M. C. Rio, France, anti-ARF6 is available from Dr. C. D'Souza-Schorey, Notre Dame, and anti-Vamp3 is available from Dr. P. Chavrier (Institute Curie, France).

In some embodiments, the microvesicles are assayed for the absence of some proteins. For example, in some embodiments the microvesicles are assayed for the absence of one or more of Vamp7, Rab8A, TfnR (transferrin receptor), cortactin, and Tks5. The absence of one or more of these proteins indicates that the population of microvesicles is invasive. In some embodiments, the absence of one or more of these proteins, combined with the presence of one or more of ARF6, Vamp3, MHC class I, MT1-MMP, β1-integrin and β1-integrin receptor indicates that the population of microvesicles is invasive.

In some embodiments, western blotting is used to identify the presence or absence of target proteins in the microvesicle population, as described below. Microvesicles can be prepared for western blotting using standard methods.

In other embodiments, immunofluorescent staining and microscopy can be used to identify the presence of target proteins using standard procedures. These methods can also be used to visualize the location and distribution of various molecules in the isolated microvesicles. For example, whole (un-lysed) microvesicles can be plated on poly-L-lysine-coated or gelatin-coated glass coverslips, and can then be fixed and processed as previously described in V. Muralidharan-Chari et al., *Cancer Res.* 69, 2201-09 (2009).

The total protein content of lysed microvesicles can be calculated, for example by using the Bradford assay (Bio-Rad). This assay utilizes a spectroscopic analysis procedure to measure the concentration of protein in a solution.

Gelatinase activity of microvesicle contents can be determined, for example using gelatin zymography. In this technique, microvesicle contents are separated on SDS-PAGE gels containing gelatin, and gelatinase activity is measured as previously described in, for example, D. H. Manicourt et al., *Anal. Biochem.* 215, 171-79 (1993).

In addition to the gelatin zymography technique, an in vitro degradation assay can also be used to assess the ability of microvesicle contents to degrade gelatin. The gelatin degradation assay has been previously described in H. Hoover et al., *Methods Enzymol.* 404, 134-47 (2005). Alternatively, isolated microvesicles can be seeded and incubated on gelatin-coated coverslips for 6-8 hours to assess their gelatin degradation potential.

Electron Microscopy (EM) can also be used to visually assess cells and microvesicles. Conventional and whole mount electron microscopy can be performed as described in, for example, G. Raposo et al., *J. Exp. Med.* 183, 1161-72 (1996). Briefly, cells grown on coverslips are fixed with 2.5% glutaraldehyde in 0.1M cacodylate buffer overnight and processed as described.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patent and literature references cited in the present specification are hereby incorporated by reference in their entirety.

EXAMPLES

Example 1

Phenotypic Variations of LOXARF6-GTP and LOXARF6-GDP Cell Lines

Figure 1B:
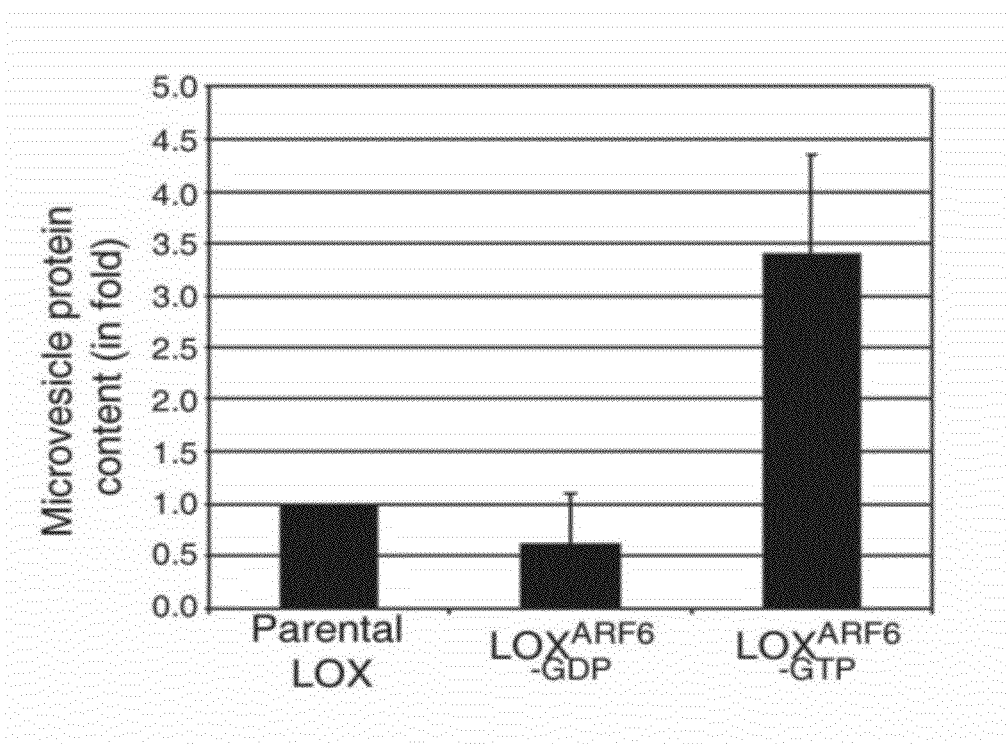
FIG. 1B shows the same results calculated by protein quantification. The average of three separate experiments is shown with standard error bars. Cell lysates were probed for ARF6 and α-tubulin by western blotting. Lower and higher molecular weight ARF6 bands in LOXARF6 cells correspond to endogenous and HA-tagged exogenous ARF6, respectively.

To investigate the mechanisms by which ARF6 promotes cell invasion, two different experimental cell lines were used, each containing a different ARF6 mutation. One cell line, called LOXARF6-GTP, stably expresses an HA-tagged, GTPase deficient ARF6 mutant referred to as ARF6-Q67L. The other cell line, called LOXARF6-GDP, stably expresses a dominant negative ARF6 mutant referred to as ARF6-T27N. In addition to these two experimental cell lines, a parental LOX cell line that expresses non-mutant ARF6 was also used. The most striking phenotype observed upon microscopic examination of LOXARF6-GDP cells was the presence of vesicle-like bulbous structures that decorate the cell surface. These structures were also seen on the surfaces of parental LOX and LOXARF6-GTP cell lines, although they were less readily obvious. Instead, in the latter two cell lines, vesicles were released into the growth medium. The lack of vesicles in the growth media of LOXARF6-GDP cells suggests that ARF6 activation is likely required for their release. When collected by low speed centrifugation of the growth media and examined for total protein or probed for ARF6 expression, vesicles shed from LOXARF6-GTP cells exhibit significantly more protein and ARF6, indicative of increased shedding from these cells relative to the parental cell line (FIG. 1A, FIG. 1B). Furthermore, mutant ARF6-GDP was not present on shed vesicles.

Figure 8:
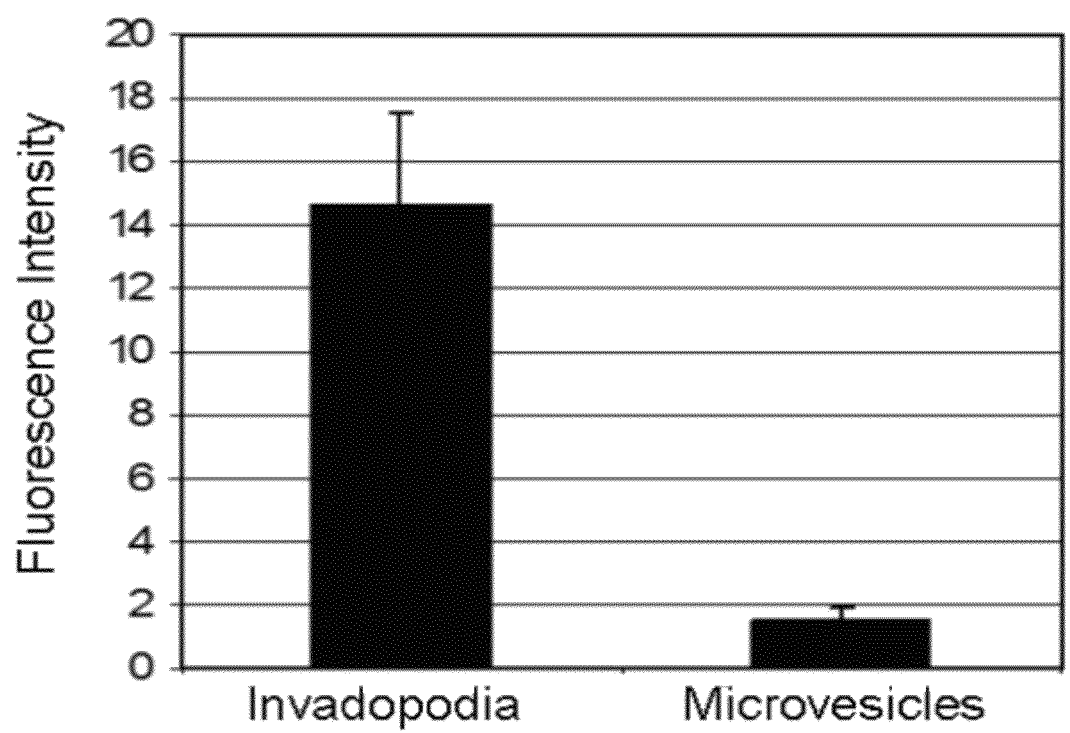
FIG. 8 shows the average fluorescence intensity of cortactin in invadopodia and microvesicles. LOX cells were plated on FITC conjugated gelatin and allowed to invade overnight. These cells were fixed and stained with anti-cortactin antibody and rhodamine phalloidin to visualize invadopodia and microvesicle structures. The fluorescence intensity of the cortactin signal was measured in invadopodia (n=56) and microvesicle structures (n=62). The signal intensity was normalized to the signal noise in an area of the slide free of cells. Error bars represent ±1 standard deviation.

LOXARF6-GTP cells were seeded on gelatin-coated coverslips, and shed microvesicles were subsequently detected in the gelatin matrix at the cell surface. Furthermore, these vesicular structures appear to be distinct from cortactin-positive invadopodia that extend into the gelatin matrix. Microvesicles do not contain cortactin, although they do contain β1 integrin, which is also present in invadopodia (E. T. Bowden et al., *Exp. Cell Res.* 312, 1240-53 (2006)). Quantitation of cortactin in microvesicles relative to cortactin in invadopodia is shown in FIG. 8. Some cells exhibit expansive membrane arbors decorated with microvesicles. Cells had a tendency to adopt this arborization phenotype, suggestive of horizontal movement when the underlying gelatin is relatively thick ($\geq 5$ µm). It is possible that cells form invadopodia at the adherent face initially and when they invade into substantial matrix and move laterally, this arbor phenotype takes effect. In contrast, LOXARF6-GDP cells appear bulbous when plated on gelatin, largely due to vesicles studded at the cell surface and little to no matrix degradation underneath the cells. As reported previously, invadopodia protrusions at the adherent surface were not observed upon expression of the dominant negative ARF6 mutant (S. E. Tague et al., *Proc. Natl. Acad. Sci.* 101, 9671-76 (2004)). Thus, ARF6 activation is coupled to two apparently distinct cellular processes linked to matrix invasion; invadopodia formation, and the release of surface vesicles into the surrounding environment.

Figure 1C:
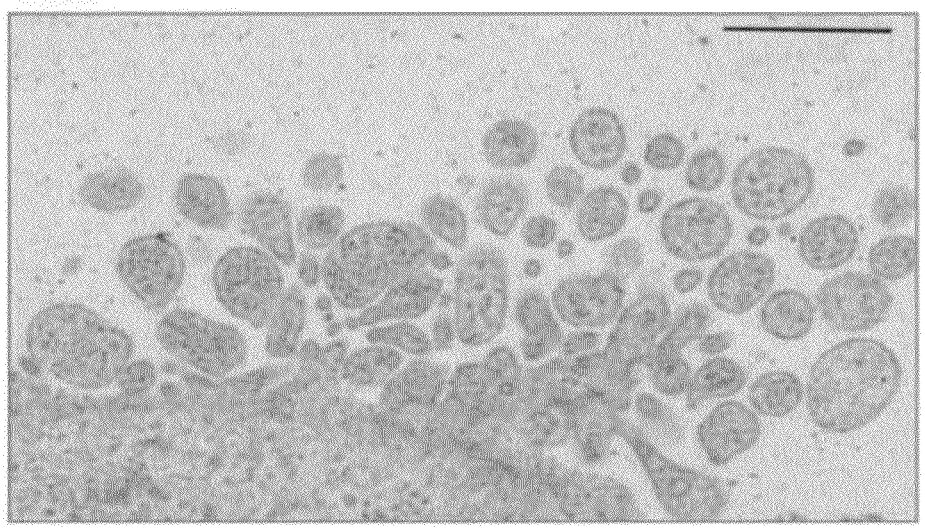
FIG. 1C shows LOXARF6-GTP and LOXARF6-GDP cell lines analyzed by electron microscopy. The image in the top panel shows heterogeneous vesicular structures near the surface of LOXARF6-GTP cells. Lower panel shows vesicular structures that appear to stud the surface of LOXARF6-GDP cells. Bar: 1000 nm.
Figure 1C:
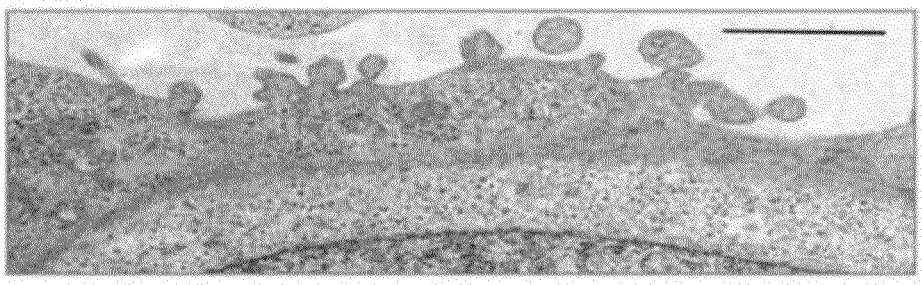

Morphological examination of LOXARF6-GTP and LOXARF6-GDP cell lines using electron microscopy (EM) suggests that vesicles at the surface of cells are heterogeneous in size (300-900 nm) (FIG. 1C). EM-based investigations also indicate that cells display no signs of nuclear fragmentation or apoptosis. All of the above suggests that the ARF6 GTPase cycle regulates the release of a heterogeneous population of vesicles from tumor cells into the surrounding environment.

Figure 1D:
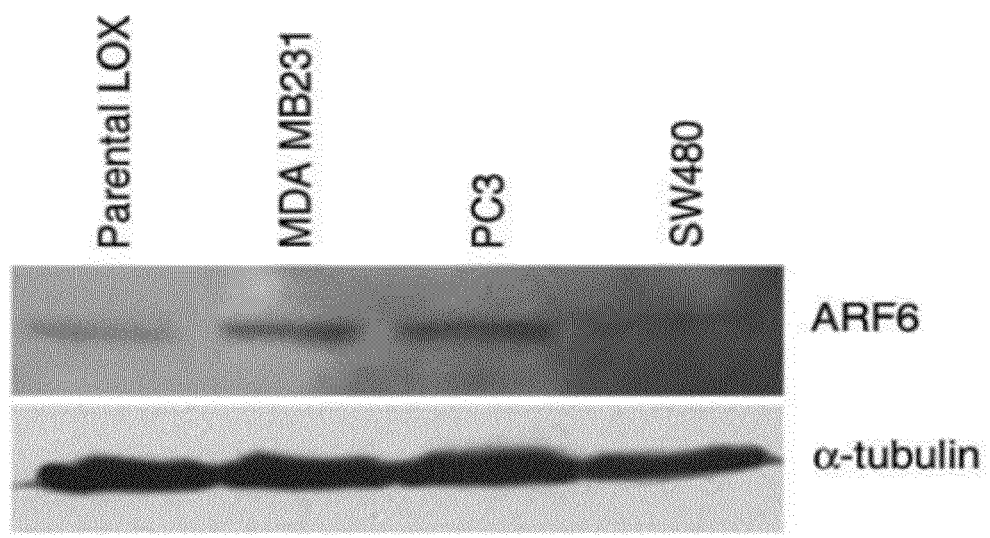
FIG. 1D shows vesicles released into the growth media from an equivalent number ($1.5 \times 10^6$ cells) of indicated tumor cell lines in culture that were isolated and probed for ARF6 by western blotting.
Figure 9A:
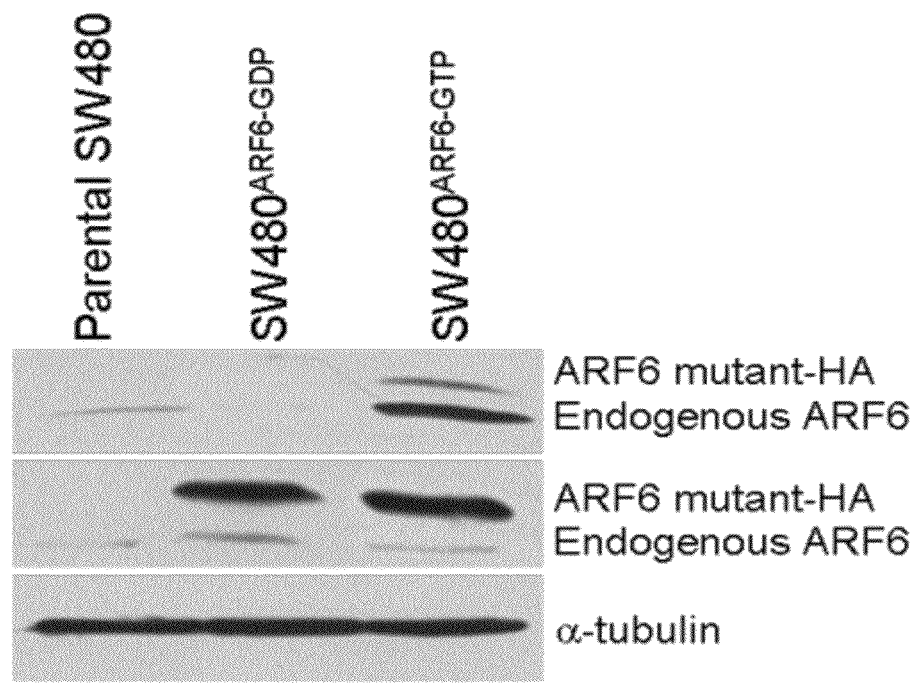
FIG. 9A depicts ARF6-mediated regulation of vesicle shedding in SW480 colon carcinoma cells. Vesicles released into the growth media from $2.2 \times 10^6$ SW480, SW480ARF6-GDP, and SW480ARF6-GTP cells were isolated by low speed centrifugation and probed for ARF6 by western blotting. Corresponding cell lysates were probed for ARF6 and α-tubulin. Low and higher molecular weight ARF6 bands correspond to endogenous and HA-tagged exogenous protein, respectively.
Figure 9B:
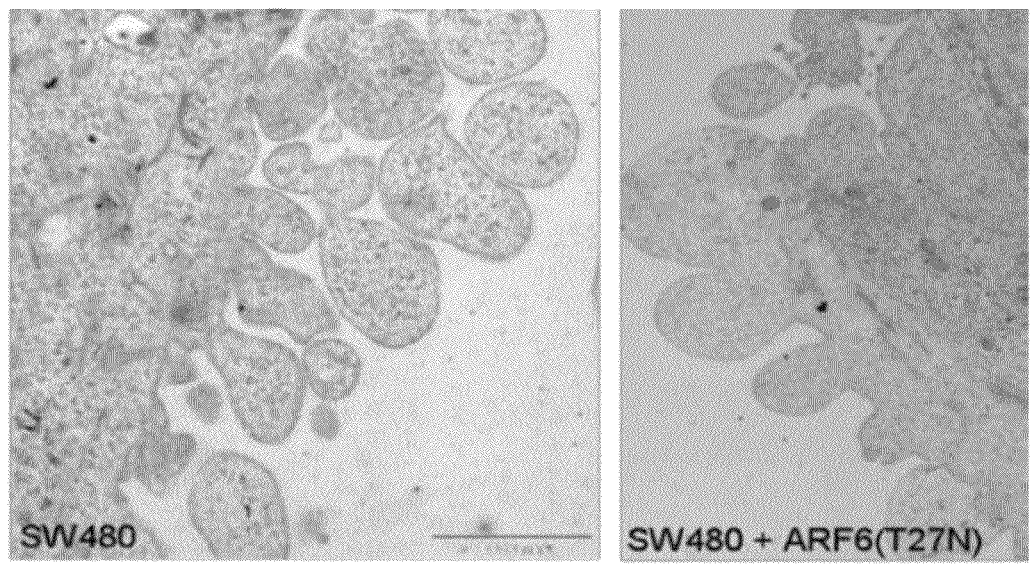
FIG. 9B also depicts ARF6-mediated regulation of vesicle shedding in SW480 colon carcinoma cells. SW480 cells with and without ARF6 (T27N) expression, as noted, were analyzed by electron microscopy. Images reveal the presence of heterogeneous microvesicle-like structures at the tumor cell surface. ARF6 (T27N) expression appears to block the microvesicle release. Bar: 1000 nm.

Vesicle shedding was examined in other tumor cell lines; SW480, a colon carcinoma cell line, PC3, a prostate adenocarcinoma cell line, and MDA-MB-231, an invasive breast tumor cell line. Gross morphological examination by phase contrast microscopy showed that shed vesicles were present in the growth media of all aforementioned cell lines. Analysis of shed vesicles collected from the growth media revealed the presence of endogenous ARF6 on isolated vesicles (FIG. 1D). Furthermore, dominant inhibition of ARF6 function by expression of ARF6-T27N in these tumor cell lines prevented vesicle release (data with SW480 cell line is shown in FIG. 9A, FIG. 9B).

Example 2

Figure 2A:
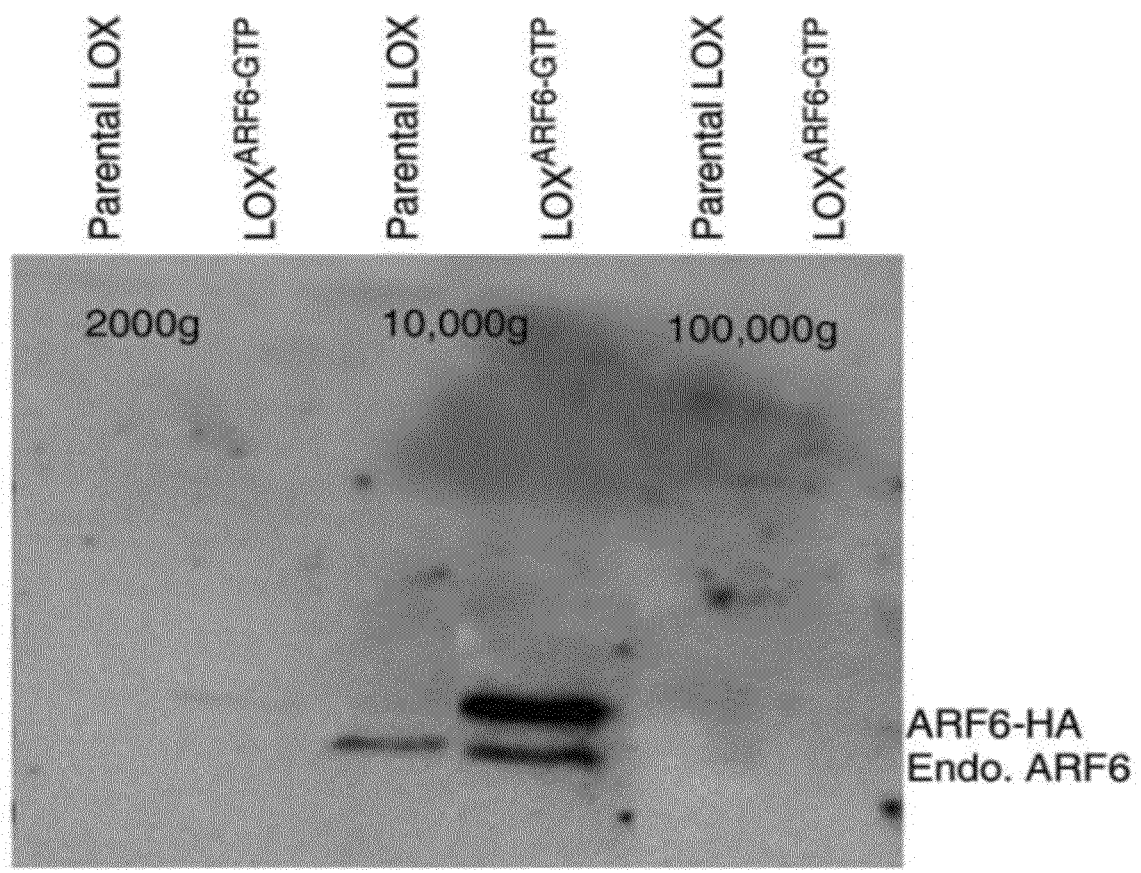
FIG. 2A shows microvesicles shed by parental LOX and LOXARF6-GTP cell lines that were fractionated as described. Equivalent amounts of protein from each fraction were probed for ARF6 content. Endogenous ARF6 and HA-tagged mutant ARF6 are enriched only in the 10,000 g fraction.
Figure 2B:
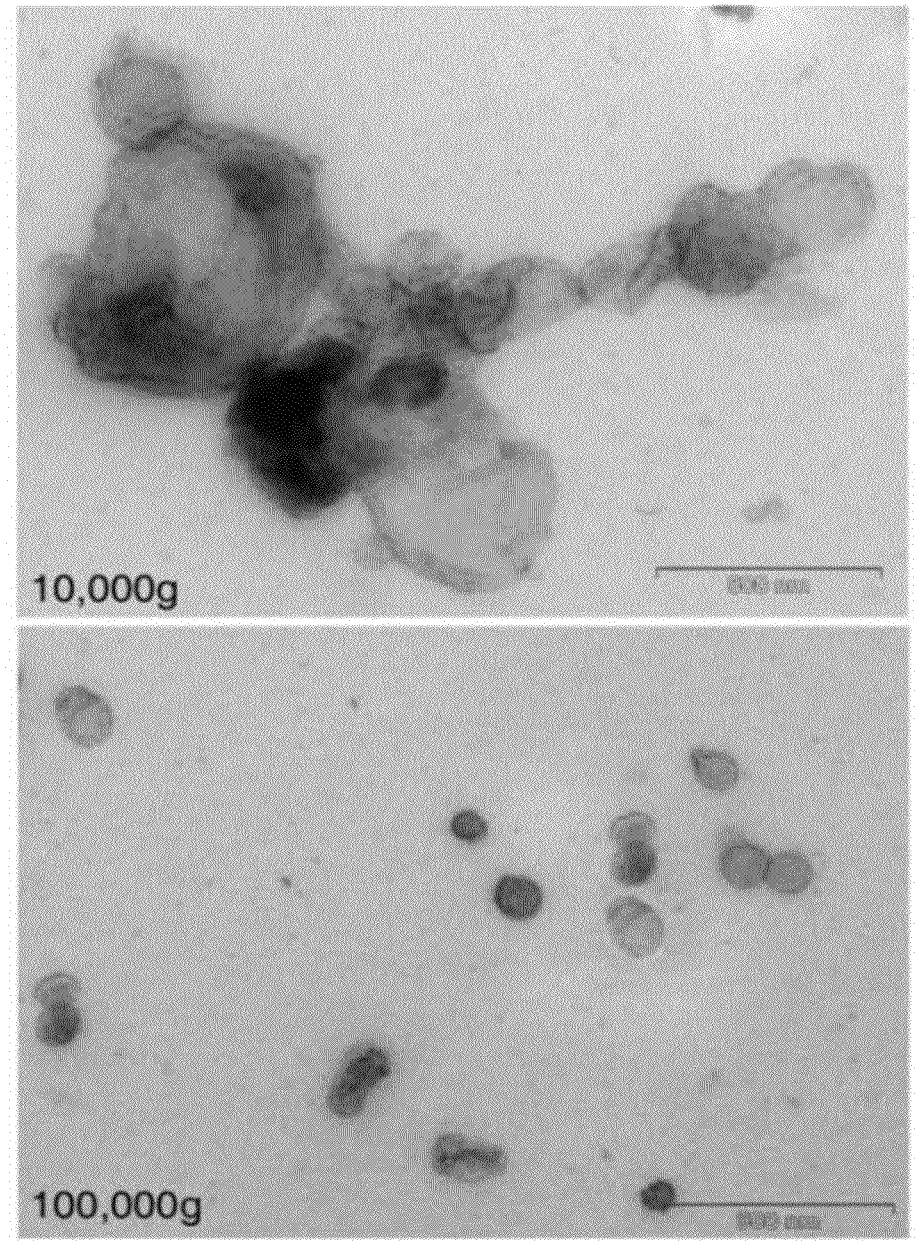
FIG. 2B shows fractionated vesicle populations isolated from LOXARF6-GTP cells analyzed by whole mount electron microscopy. Microvesicles isolated in the 10,000 g fraction are larger (300-900 nm) and heterogeneous relative to the more uniform 50-70 nm vesicles in the 100,000 g fraction, typical of exosomes. Bar: 500 nm.

ARF6-GTP Facilitates the Release of Plasma Membrane-Derived Microvesicles into the Surrounding Environment There is accruing evidence for the existence of unconventional secretory mechanisms, such as the release of exosomes and microvesicles, that do not utilize the classical signal-peptide secretory transport pathway. Exosomes are internal vesicles of multivesicular bodies/late endosomes that are released upon exocytosis (B. Fevrier et al., *Curr. Opin. Cell Biol.* 16, 415-21 (2004)). Morphological characterization of ARF6-regulated shed vesicles suggests that they are microvesicles. Isolated ARF6-positive vesicles pellet by centrifugation at approximately 10,000 g, unlike exosomes, which sediment by centrifugation at approximately 100,000 g. FIG. 2A shows that ARF6-positive vesicles are not present in the 100,000 g fraction. Ultrastructural analyses of whole mount preparations of the 10,000 g and 100,000 g fractions confirmed the heterogeneity of the 10,000 g microvesicles relative to the more uniform 50-70 nm vesicles characteristic of exosomes in the 100,000 g fraction (FIG. 2B).

Studies have shown that phosphatidylserine (PS) externalization accompanies shedding of plasma membrane-derived microvesicles (B. Hugel et al., *Physiology* (Bethesda) 20, 22-27 (2005)). Externalization of PS on the surface of microvesicles based on reactivity with Annexin-V, a high affinity PS-binding protein, has been found in some studies. This was particularly evident in LOXARF6-GDP cells, where microvesicles stud the cell surface. These microvesicles are not apoptotic bodies. As stated above, expression of mutant ARF6 in LOX cells does not induce morphological changes such as condensed chromatin and pyknotic nuclei. In addition, data from expression of mutant ARF6 in LOX cells does not indicate that cleaved caspase 3 is present in the cells. On the other hand, when treated with okadaic acid, a known inducer for apoptosis, experimental data indicates that cleaved caspase 3 is present in a higher proportion of the cells. Accordingly, these data suggest that ARF6 activation facilitates the release of microvesicles.

Example 3

Shed Microvesicles Contain Proteases and Facilitate ECM Degradation

Figure 3A:
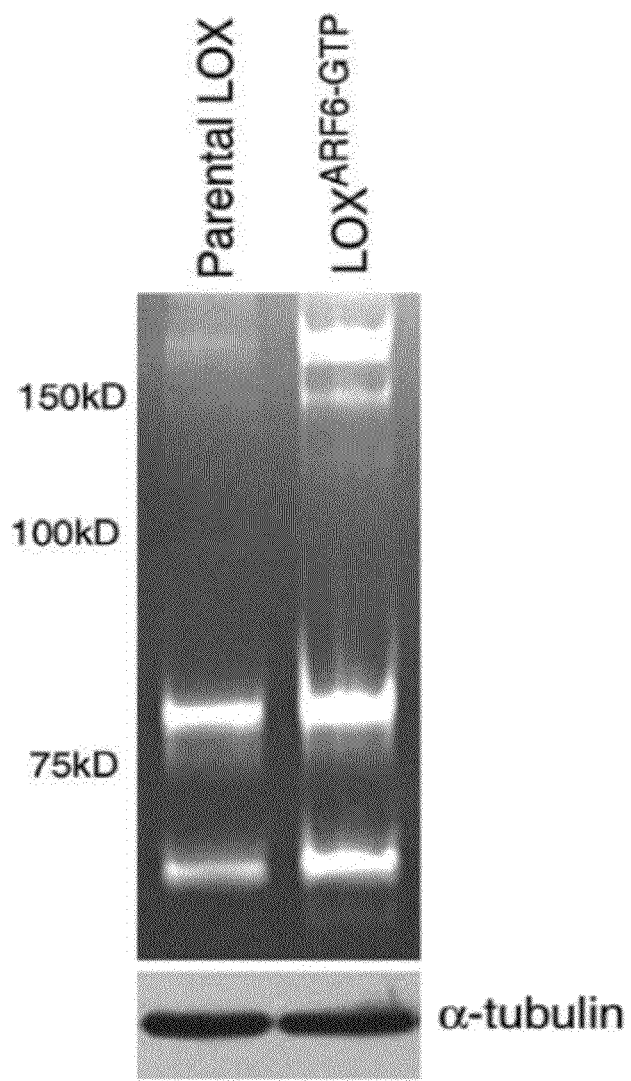
FIG. 3A shows microvesicles shed from an equal number of parental LOX and LOXARF6-GTP cells. The cells were isolated, and microvesicle lysates were analyzed by gelatin zymography. Cell lysates were probed for α-tubulin expression. High and low molecular weight gelatinases are present in microvesicle lysates.

Previous studies have shown that microvesicles shed by breast carcinoma and ovarian cancer cell lines contain proteases, including matrix metalloproteinases, such as MMP-2 and MMP-9 (V. Dolo et al., *Cancer Res.* 58, 4468-74 (1998)). ARF6-positive microvesicles obtained from a 10,000 g fraction collection procedure contained high and low molecular weight gelatinases, as indicated by gelatin zymography (FIG. 3A), and MT1-MMP. Notably, MT1-MMP silencing significantly decreases the basal invasiveness of experimental cell lines. Moreover, shed microvesicles, when seeded on FITC-gelatin, were capable of matrix degradation, which appeared as dark spots around microvesicle membranes.

Some researchers believe that β1 integrins facilitate interaction of shed microvesicles with the ECM, and that vesicle contents are released after microvesicle bursting induced by acidic pH of the tumor environment (G. Taraboletti et al., *Neoplasia* 8, 96-103 (2006)). The addition of inactivating β1 integrin antibody, AIIB2, to isolated microvesicles or experimental cell lines blocked adhesion and matrix degradation, suggesting that protein topology in the microvesicle membrane is still maintained and that integrin receptor association with extracellular matrix is important for microvesicle-mediated matrix degradation AIIB2 binds to and therefore labels the extracellular surface of both cells and shed microvesicles, indicating that β1 integrin is a component of the microvesicle membrane. Thus, while proteases at the invadopodia surface facilitate pericellular proteolysis in the immediate vicinity of the cell, shed microvesicles containing proteases may travel away from the immediate cellular vicinity and facilitate proteolysis at distal locations. Microvesicle release could therefore provide a mechanism for rapid and directed proteolysis that creates a path of diminished resistance for cell migration.

Example 4

Selective Sorting of Cargo into Cell Surface Microvesicles

Figure 3B:
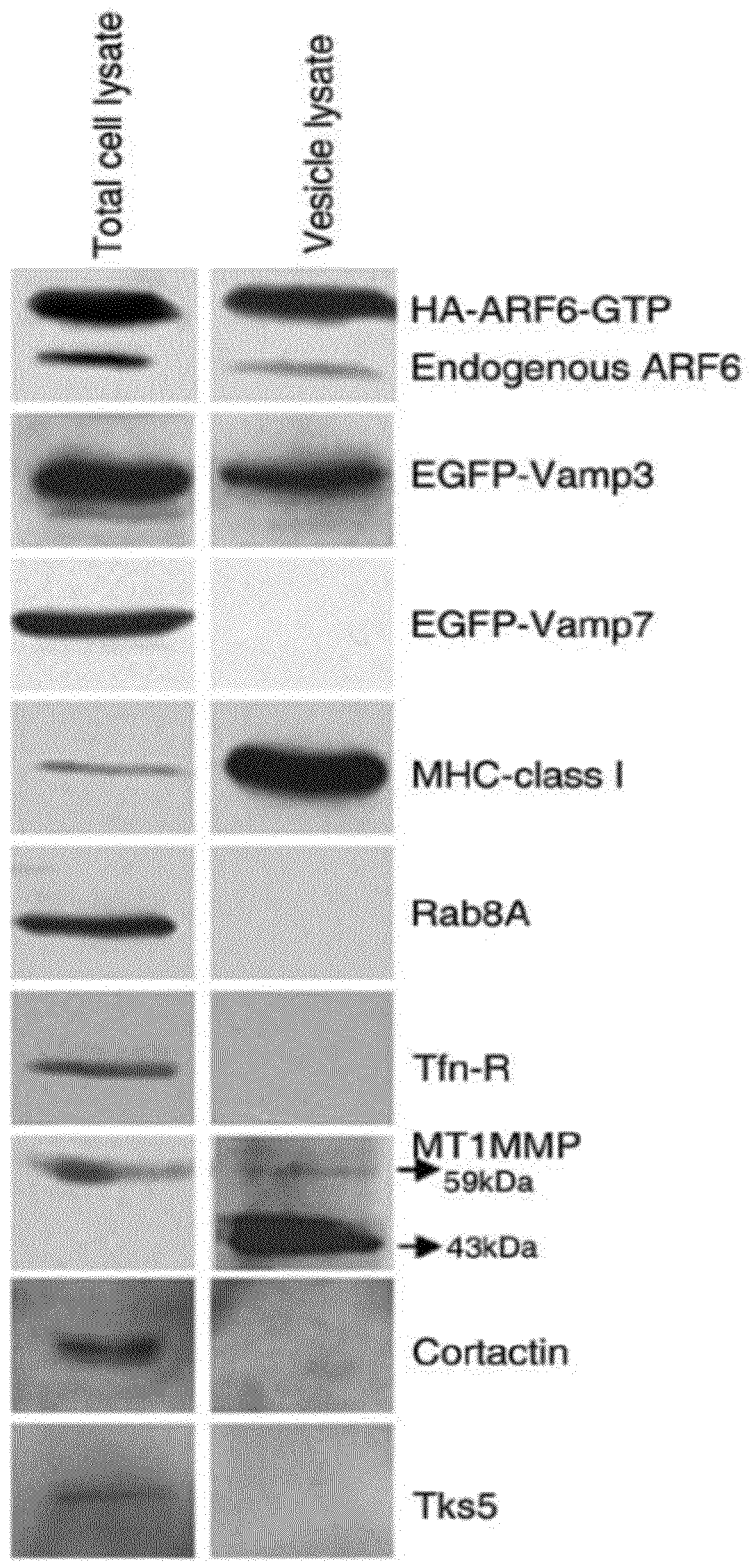
FIG. 3B shows lysates of LOXARF6-GTP cells or of shed microvesicles that were analyzed for indicated endogenous proteins or transfected proteins (EGFP-VAMP3 or EGFP-VAMP7) by western blotting.

Besides proteases, microvesicles have been shown to be selectively enriched in β1 integrin receptors and MHC class I molecules (MHC-I). Both MHC-I molecules and integrin receptors traffic to and from the plasma membrane via ARF6-regulated endosomal compartments (J. G. Donaldson, *J. Biol. Chem.* 278, 41573-76 (2003)). Microscopic examination shows that MHC-I in LOXARF6-GDP cells is present in the perinuclear compartments and the cell surface, but largely at the cell surface in LOXARF6-GTP cells. Western blotting analysis of shed vesicles reveals that, along with endogenous ARF6, MHC-I, β1 integrin, VAMP 3, and MT1-MMP were also present in microvesicles (FIG. 3B). Of note, processed forms of MT1-MMP are present in the microvesicles. However, microvesicles were devoid of transferrin receptors, VAMP7, or Rab8A, as well as cortactin and TksS, which are known components of invadopodia. Thus, cargo trafficked via recycling of endosomes to the cell surface appears to be selectively sorted into these surface microvesicles.

Example 5

ARF6-GTP-Induced Microvesicle Shedding Involves the Extracellular Signal Regulated Kinase (ERK)

Figure 4A:
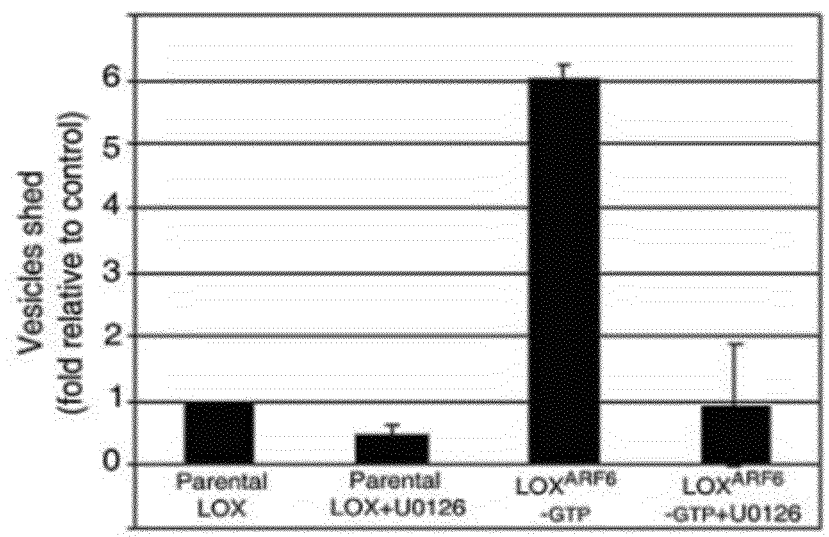
FIG. 4A shows parental LOX and LOXARF6-GTP cell lines that were treated with 30 μM U0126 and microvesicles shed into the media that were isolated and quantitated for protein. Data from 5 independent experiments is plotted. Standard error bars are shown.

ARF6-enhanced melanoma cell invasion is dependent on the activation of the extracellular signal-regulated kinase (ERK) (S. E. Tague et al., *Proc. Natl. Acad. Sci.* 101, 9671-76 (2004)). Moreover the ARF6 GTPase cycle regulates ERK activation (S. E. Tague et al., *Proc. Natl. Acad. Sci.* 101, 9671-76 (2004), S. E. Robertson et al., *Mol. Biol. Cell* 17, 645-57 (2006), J. S. Tushir et al., *Embo. J.* 26, 1806-19 (2007)) downstream of c-Raf/A-Raf (E. Nekhoroshkova et al., *PLoS ONE* 4(2): e4647 (2009)). Therefore, ARF6-GTP-induced microvesicle shedding was investigated to determine if it is also dependent on ERK signaling. Treatment of parental LOX and LOXARF6-GTP cells with U0126, an inhibitor of MEK, the kinase immediately upstream of ERK, resulted in significant inhibition of basal as well as ARF6-GTP enhanced microvesicle shedding (FIG. 4A). Upon MEK inhibition, both parental LOX and LOXARF6-GTP accumulated microvesicles at the cell surface that resembled the LOX-ARF6-GDP phenotype. Similarly, MEK inhibition also blocked microvesicle shedding from PC3 and SW480 cell lines. Thus, ARF6-regulated microvesicle shedding requires ERK.

Figure 4B:
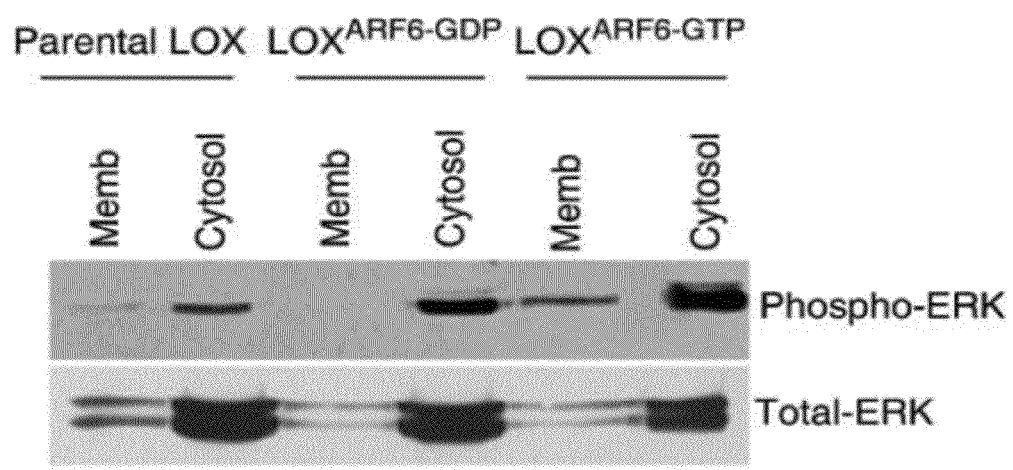
FIG. 4B shows parental LOX, LOXARF6-GDP, and LOX-ARF6-GTP cells that were subjected to subcellular fractionation. The amount of endogenous phospho-ERK and total-ERK in the membrane and cytosolic fractions was analyzed by immunoblotting.

Consistent with earlier findings in HeLa cells (S. E. Robertson et al., *Mol. Biol. Cell.* 17, 645-57 (2006)), ERK localizes to the cytoplasm in LOXARF6-GDP cells. In contrast, membrane-associated ERK is predominantly at the cell surface in LOX and LOXARF6-GTP cells. This becomes further evident in sub-cellular fractionation studies, wherein the activated phospho-ERK distribution is significantly greater in the membrane fraction of LOXARF6-GTP cells (FIG. 4B). Thus, ARF6 activation likely enhances ERK redistribution to the plasma membrane, which in turn facilitates its phosphorylation and microvesicle release.

Example 6

ARF6-Regulated ERK Activation Involves Phospholipase D

Figure 5A:
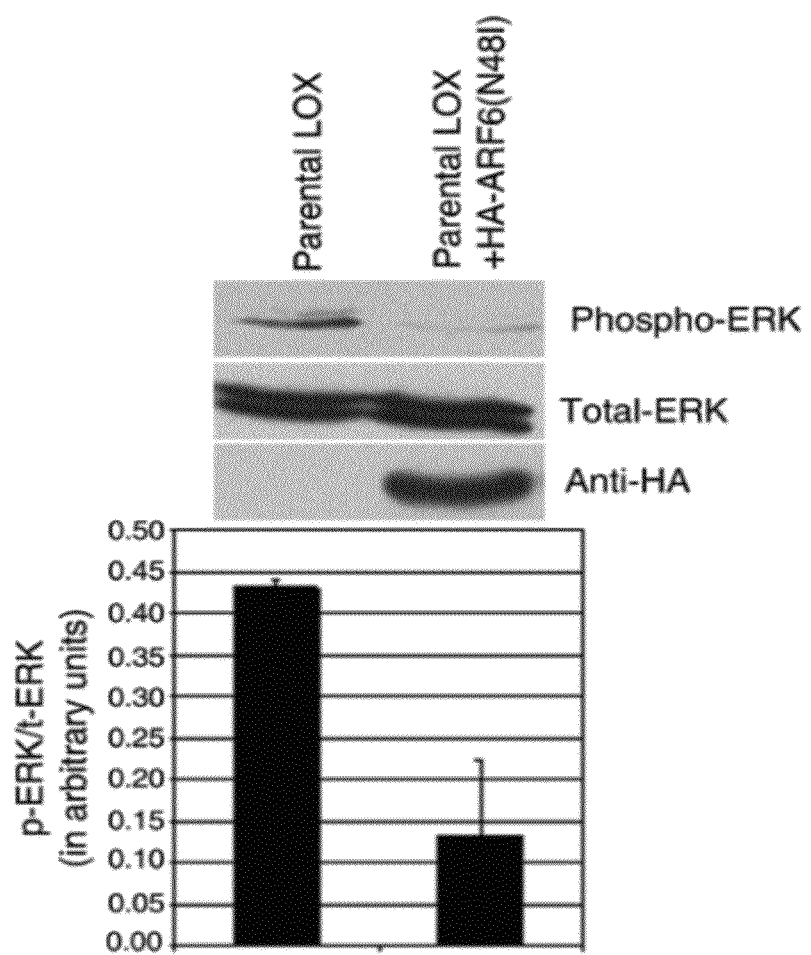
FIG. 5A shows lysates of LOX cells that were transiently transfected with HA-tagged-ARF6-N48I mutant protein. The cells were probed for phospho-ERK and total ERK by western blotting. The data is representative of 3 separate experiments. Band intensities were quantified by densitometry, and the ratio of phospho-ERK to total ERK is shown.
Figure 5B:
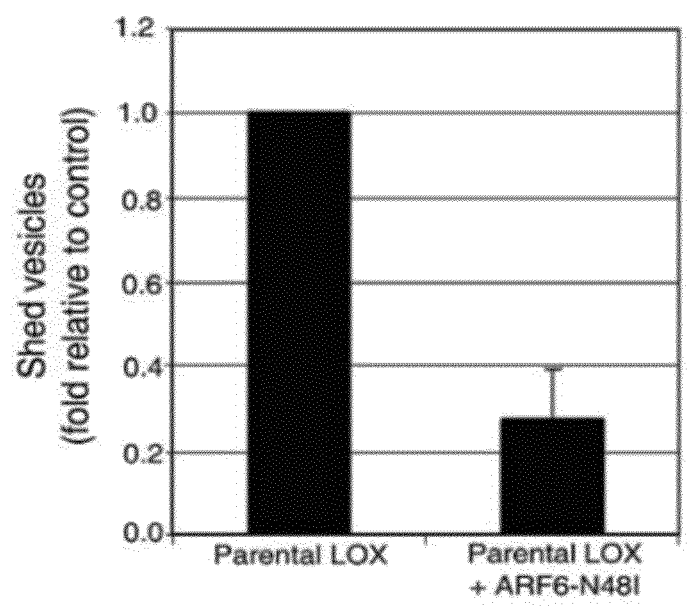
FIG. 5B shows microvesicles released into the media by parental LOX and LOX cells transfected with ARF6-N48I. Microvesicles were isolated by differential centrifugation and quantitated for protein content. The average of four separate experiments with standard error bars is shown. Microvesicles in the growth media of cells expressing ARF6-N48I is lower relative to non-transfected controls.
Figure 5C:
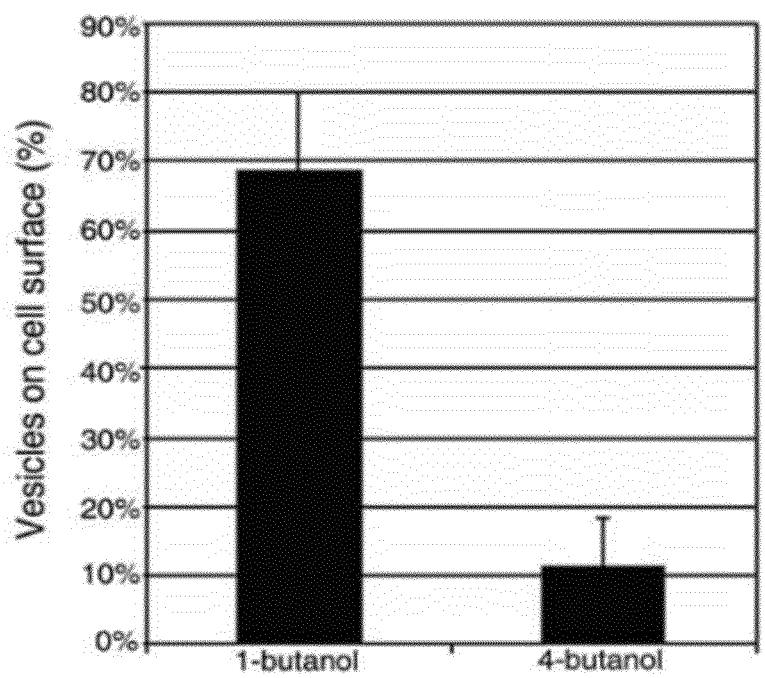
FIG. 5C shows LOX cells that were treated with 0.3% t-butanol or 1-butanol for 30 min, and then fixed and stained for actin to visualize surface-associated microvesicles. For each experimental condition, cells that showed eight or more microvesicles at the surface were scored, and the percent inhibition of vesicle shedding was determined. 250 cells were observed for each experiment, and the data from four independent experiments is plotted. Standard error bars are shown.

Studies have shown that ARF6 stimulates phospholipase D (PLD) activity (C. D'Souza-Schorey et al., *Nat. Rev. Mol. Cell Biol.* 7, 347-58 (2006)). Further, PLD has been shown to facilitate ERK activation. Here, ARF6 regulated PLD activity and its involvement with ERK activation was tested. First, phospho-ERK levels upon PLD inactivation were examined. The results show that expression of ARF6-N48I, an ARF6 mutant defective in PLD activation, inhibits ERK activation (FIG. 5A) and microvesicle shedding (FIG. 5B). PA levels were significantly decreased in ARF6-N48I-expressing cells, and ERK distribution was found in intracellular cytoplasmic structures. Next, primary alcohols were used to inhibit PLD, which results in the formation of phosphatidylalcohol at the expense of phosphatidic acid by replacing water. The results show that treatment of cells with 1-butanol also inhibits ERK activation and microvesicle shedding (FIG. 5C). Thus, PLD activation is upstream of ERK activation and is therefore involved with ARF6-regulated microvesicle shedding.

Figure 5D:
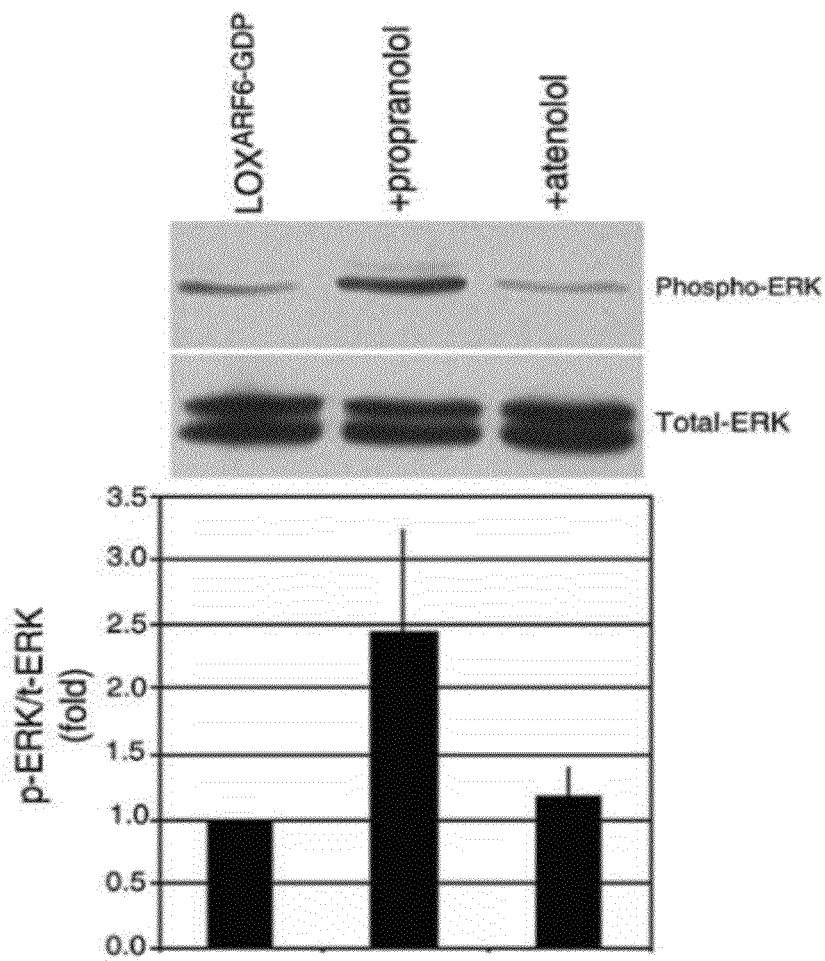
FIG. 5D shows lysates of LOXARF6-GDP cells treated with propranolol (0.1 mM) and atenolol (10 uM). The treated cells were probed for phospho-ERK and total-ERK. Band intensities were quantified by densitometry. The average of 3 independent experiments is plotted and standard error bars are shown.
Figure 5E:
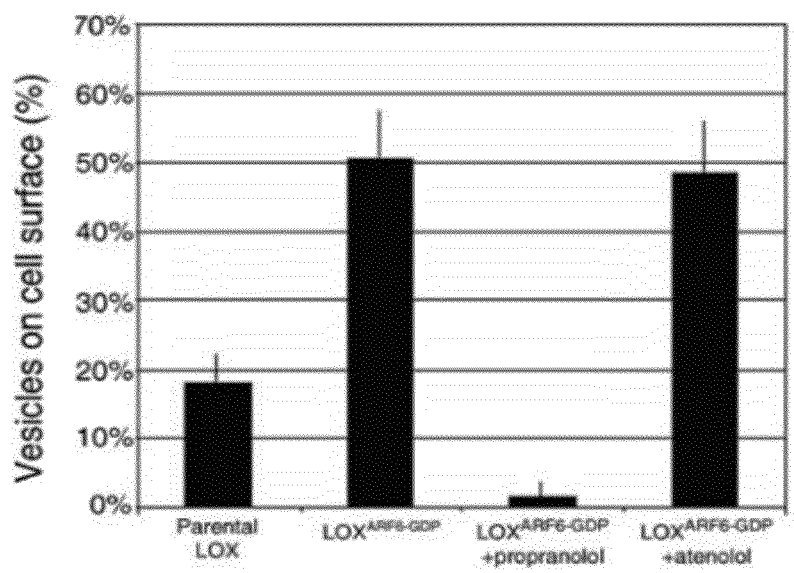
FIG. 5E shows LOXARF6-GDP cells treated with propranolol or atenolol. The treated cells were visualized, and those with microvesicles present at the cell surface were scored as described above. Propranolol-treatment of LOXARF6-GDP cells restored vesicle shedding.

Next, the role of phospho-ERK levels in microvesicle shedding was investigated. Specifically, microvesicle shedding was examined in LOXARF6-GDP cells after phospho-ERK levels were restored, or after stimulating PLD activity through pathways independent of ARF6. Treatment with propranolol, a PA phosphohydrolase inhibitor (O. A. Jovanovic et al., *Mol. Biol. Cell* 17, 327-35 (2006)), restored phospho-ERK levels in LOXARF6-GDP cells, as shown in FIG. 5D and induced microvesicle shedding in LOXARF6-GDP cells (FIG. 5E). Unlike propranolol, another GCPR antagonist, atenolol, did not have any effect on phospho-ERK levels or microvesicle release (FIG. 5D, FIG. 5F). These data corroborate the involvement of PLD and ERK activation in regulating microvesicle shedding. Finally, the effect of 1-butanol on microvesicle shedding induced by expression of constitutively activated MEK was investigated. Activated MEK increases microvesicle shedding more than 12-fold compared to the parental LOX cells; however, 1-butanol had little to no effect on microvesicle shedding, confirming that ERK lies downstream of PLD activation.

Example 7

ERK Facilitates Microvesicle Shedding by Phosphorylating Myosin Light Chain

Figure 6A:
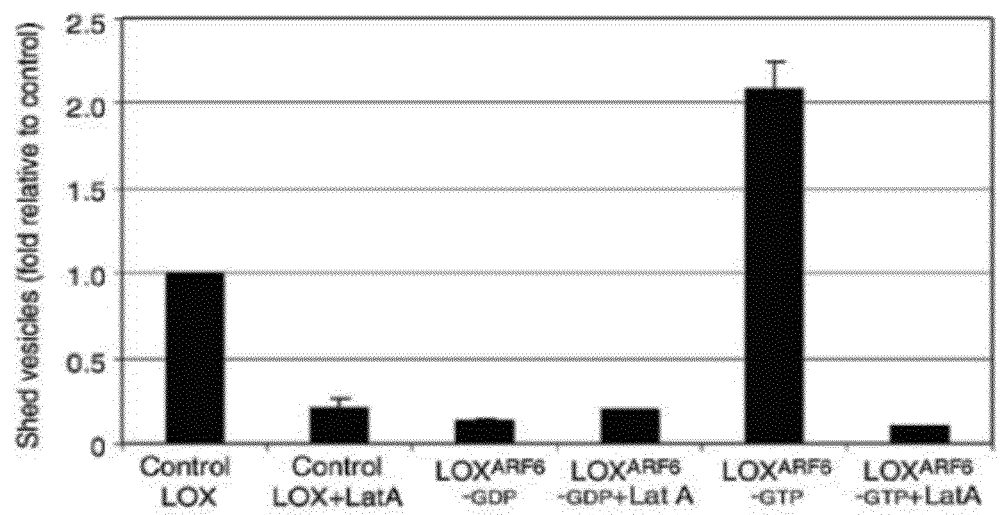
FIG. 6A shows parental LOX, LOXARF6-GTP, and LOX-ARF6-GDP cells in culture that were incubated with fresh media containing 2 μM Latrunculin A (Lat A) for 45 min. Released microvesicles were isolated and quantitated for protein. The average of three independent experiments with standard error bars for each experimental condition is shown.

Treatment of LOX cells with blebbistatin, a small molecule inhibitor of myosin II activity, or with latrunculin A, an actin-binding toxin that inhibits actin polymerization, profoundly affected microvesicle shedding. In the presence of blebbistatin, microvesicles do not form. 85-90% of latrunculin A treated cells exhibited clustered microvesicles at the cell surface. Accordingly, latrunculin A treatment also inhibited the release of microvesicles from both parental LOX and LOX-ARF6-GTP cells (FIG. 6A). Thus, microvesicle shedding is likely mediated via an actomyosin-dependent mechanism. MLCK, a $Ca^{2+}$/calmodulin-dependent kinase, phosphorylates myosin II light chain (MLC) to promote contraction of the actin-based cytoskeleton (A. Sobieszek et al., *Biochem. J.* 295 (Pt 2), 405-11 (1993)). ERK has been shown to phosphorylate MLCK, which in turn phosphorylates MLC at Thr18/Ser19 and thereby stimulates MLC activity (R. L. Klemke et al., *J. Cell Biol.* 137, 481-92 (1997), D. H. Nguyen et al., *J. Cell Biol.* 146, 149-64 (1999)). ARF6-GTP-induced ERK activation at sites of vesicle release was tested, and the results indicate that it leads to localized activation of MLCK, which in turn stimulates serine phosphorylation of MLC to allow force generation required for microvesicle fission. In support of this contention, immunofluorescent labeling of LOX tumor cells revealed that phospho-MLC localizes to the "necks" of microvesicles at the cell surface.

Figure 6B:
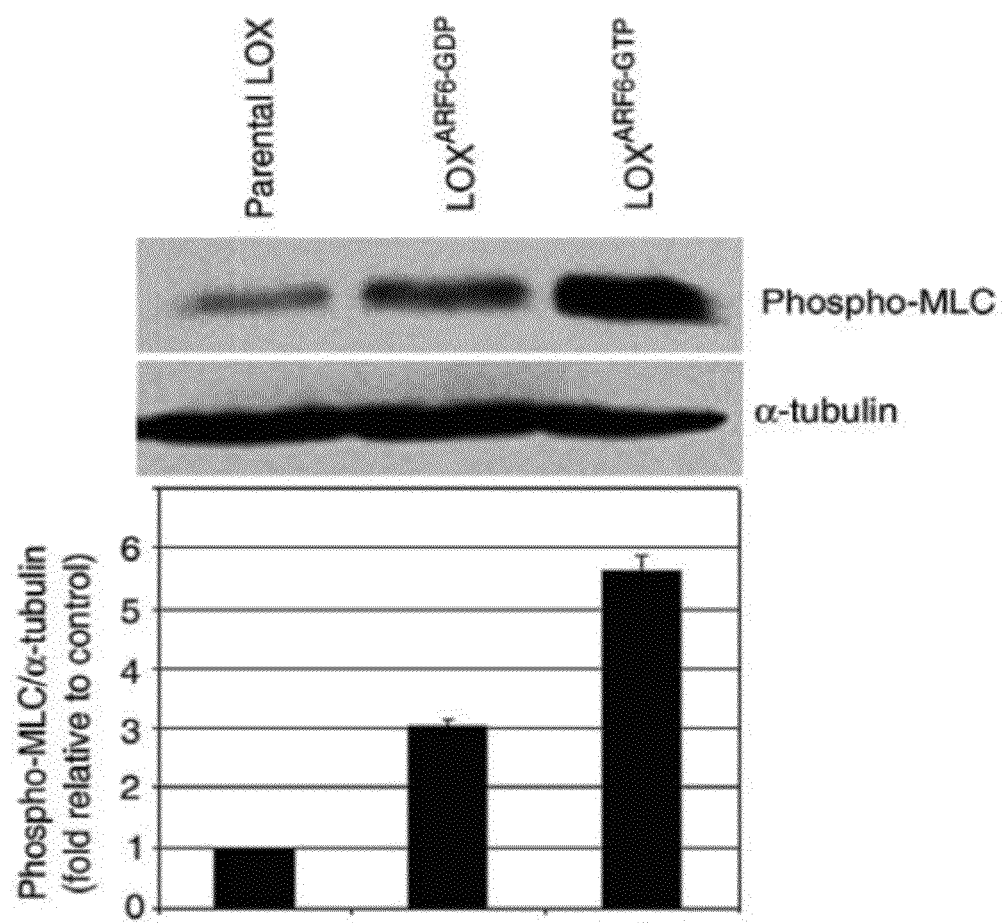
FIG. 6B shows cell lysates of LOX, LOXARF6-GTP, and LOXARF6-GDP cell lines that were analyzed for endogenous phospho-MLC by western blotting. α-tubulin expression was also assessed as an indicator for equal loading. Band density was measured by densitometric scanning.
Figure 10A:
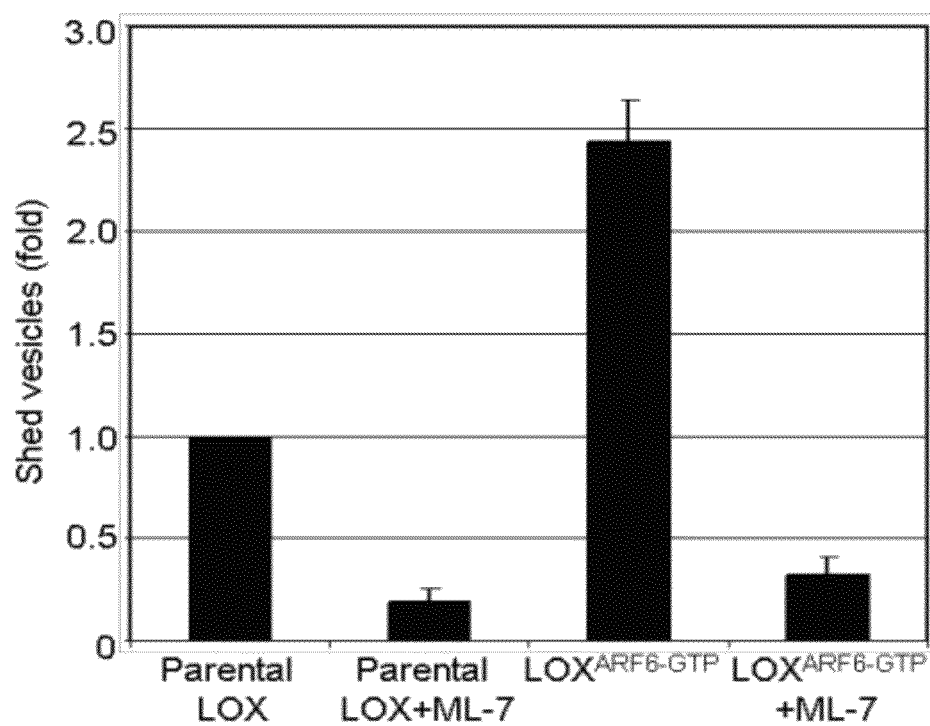
FIG. 10A shows that MLC phosphorylation is required for microvesicle shedding in parental LOX and LOXARF6-GTP cells. Parental LOX and LOXARF6-GTP were treated with 10 μM ML-7 for 2 hrs. Microvesicles released were isolated, quantitated for protein, and the data is shown as fold change in shedding relative to untreated LOX cells. MLC phosphorylation is blocked by the MLCK inhibitor in LOX and LOX-ARF6-GTP cells but not in LOXARF6-GDP cells.
Figure 10B:
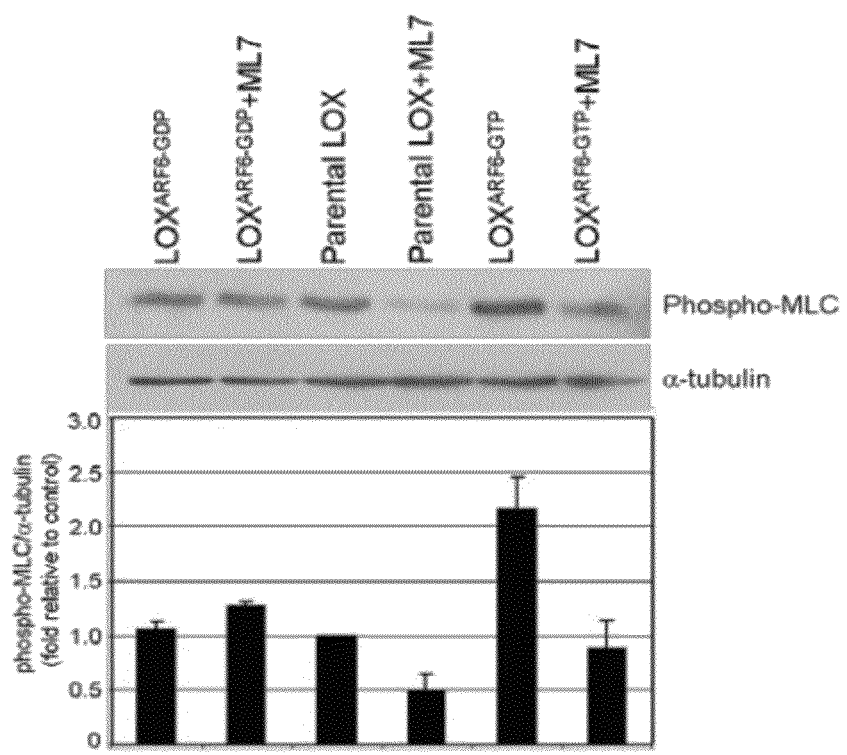
FIG. 10B shows MLCK-dependent phosphorylation of MLC in parental LOX and LOXARF6-GTP cells, but not in LOXARF6-GDP cells. Cell lines as indicated were treated with ML-7, and cell lysates were probed for phospho-MLC and α-tubulin by Western blotting. Band density was measured by densitometric scanning. Fold increase in the ratio of phospho-MLC to α-tubulin in ML-7 treated cells relative to untreated cells is shown.
Figure 10C:
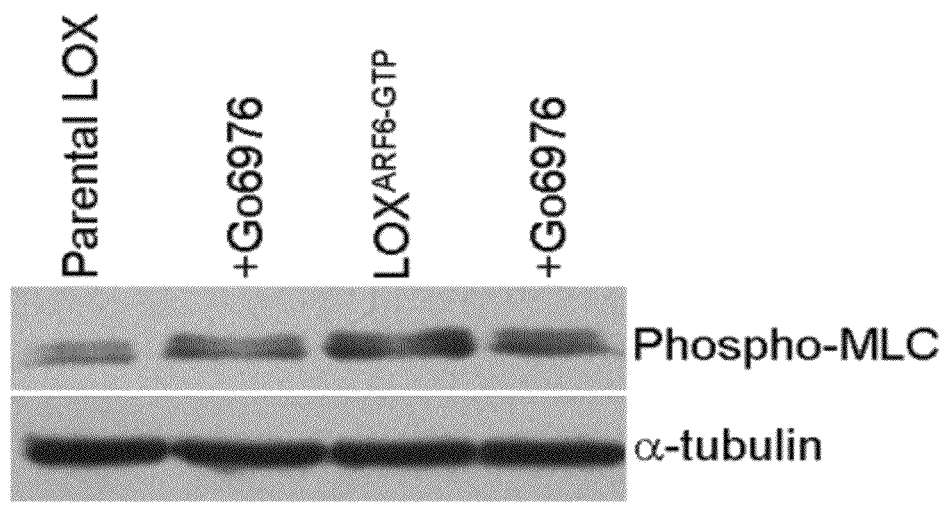
FIG. 10C shows that MLC phosphorylation is independent of PKC in parental LOX and LOXARF6-GTP cells. Lysates of parental LOX and LOXARF6-GTP treated with Go6976 (10M) for 2 hrs at 37° C. were probed for phospho-MLC and α-tubulin by Western blotting.

Phosphorylation of MLC was examined in parental LOX and LOX mutant lines by western blotting. As shown in FIG. 6B, levels of phospho-MLC are significantly increased in LOXARF6-GTP cells compared to parental LOX cells. Treatment of parental LOX and LOXARF6-GTP cells with ML-7, an MLCK inhibitor, blocks MLC phosphorylation as well as microvesicle shedding (FIG. 10A, FIG. 10B, FIG. 10C). Taken together, these data indicate that ARF6 facilitates microvesicle fission via a mechanism that involves ERK-dependent MLC phosphorylation.

Figure 6C:
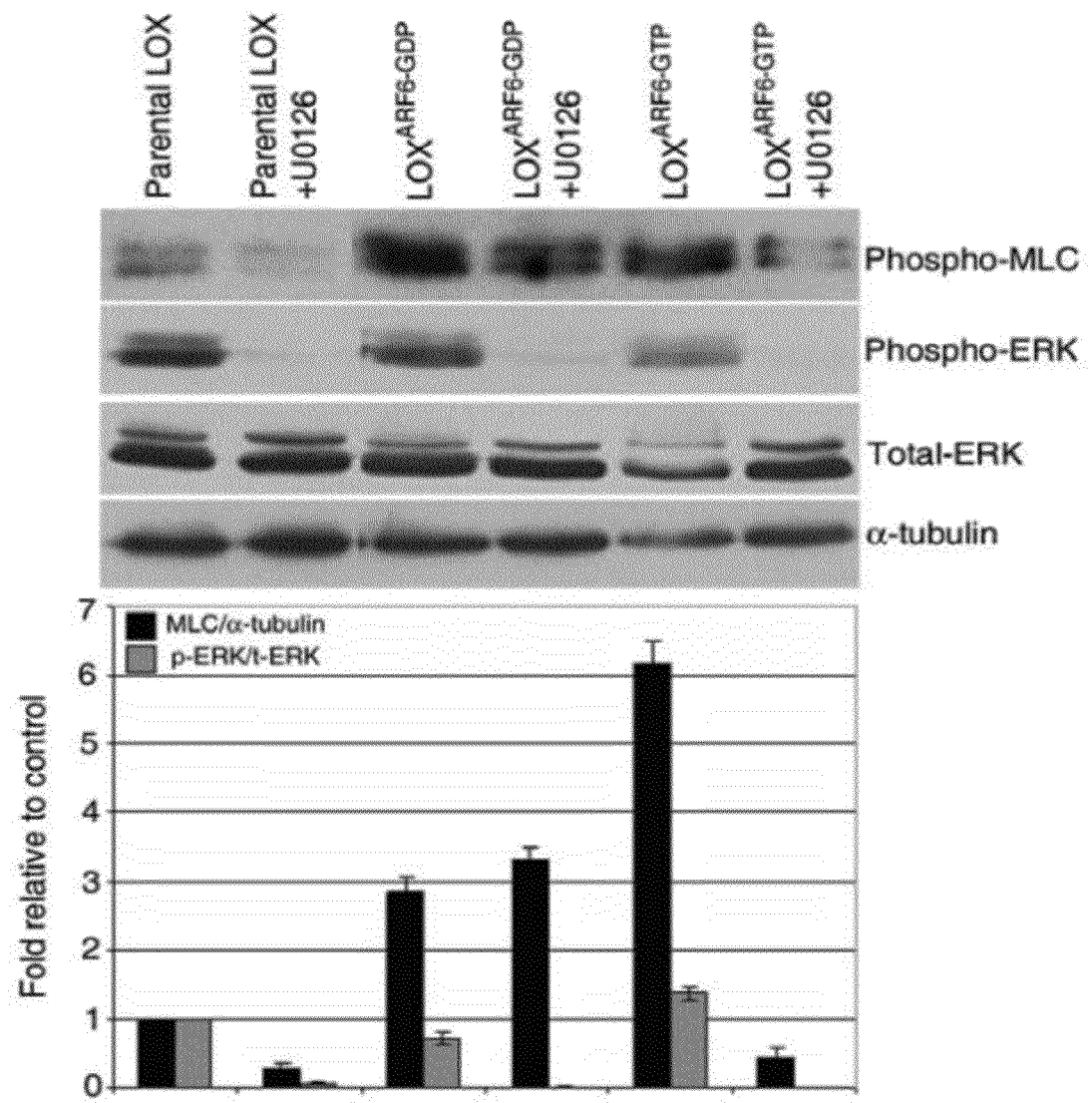
FIG. 6C shows lysates of LOX cells treated with U0126 (30 μM) that were analyzed for endogenous phospho-MLC, phospho-ERK, total-ERK, and α-tubulin by western blotting. Additional lanes on the immunoblot between lanes 2 and 3 were spliced out. Band density was measured by densitometric scanning.

As seen in FIG. 6B, no decrease in phospho-MLC levels was observed in LOXARF6-GDP cells. In fact, phospho-MLC levels in LOXARF6-GDP cells were slightly higher than basal levels. A possible explanation for this observation is that the phosphorylation of MLC in LOXARF6-GDP cells is "inhibitory" and independent of ERK. To investigate this further, the levels of phospho-MLC in the presence and absence of U0126 were compared in parental LOX and LOX mutant lines. As seen in FIG. 6C, inhibition of phospho-MLC was evident in the presence of MEK inhibitor in parental LOX and in LOXARF6-GTP cells, but there was no inhibition in phospho-MLC levels in LOXARF6-GDP cells. Also, treatment with ML7 had little to no effect on MLC phosphorylation in LOXARF6-GDP cells (FIG. 10A, FIG. 10B, FIG. 10C). This further confirms that the phosphorylation of MLC in LOXARF6-GDP cells is not mediated by ERK.

Figure 6D:
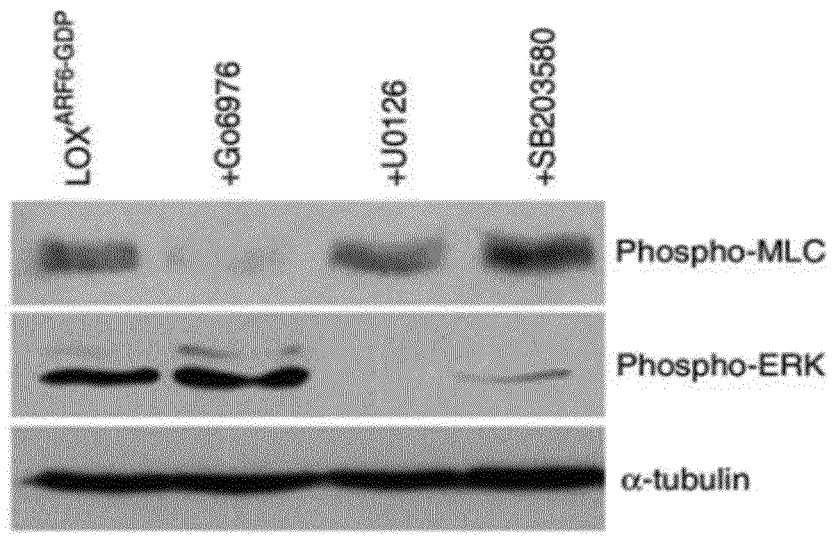
FIG. 6D shows LOXARF6-GDP cells that were treated with the following inhibitors: Go6976 (PKC inhibitor-10 μM), ML-7 (MLCK inhibitor-10 μM), U0126 (MEK inhibitor-30 μM) and SB203580 (p38 inhibitor-10 μM) for 2 hrs at 37° C. Cell lysates were probed for phospho-MLC, phospho-ERK and α-tubulin by western blotting.
Figure 7A:
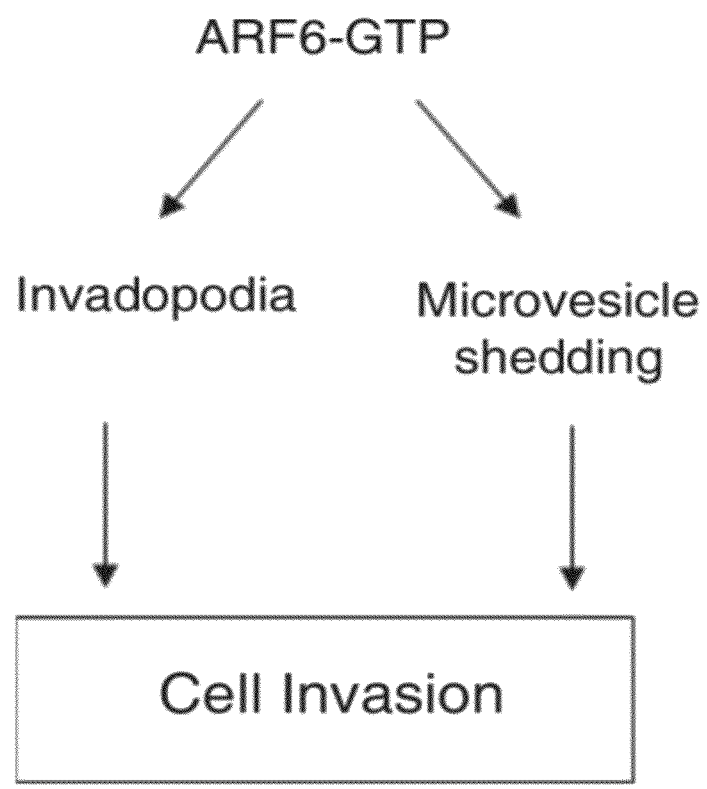
FIG. 7A depicts a working model for ARF6-mediated regulation of cell invasion. In this model, activated ARF6 facilitates tumor cell invasion by promoting invadopodia formation and microvesicle shedding. The formation of invadopodia and microvesicle release requires ARF6 and ERK.
Figure 7B:
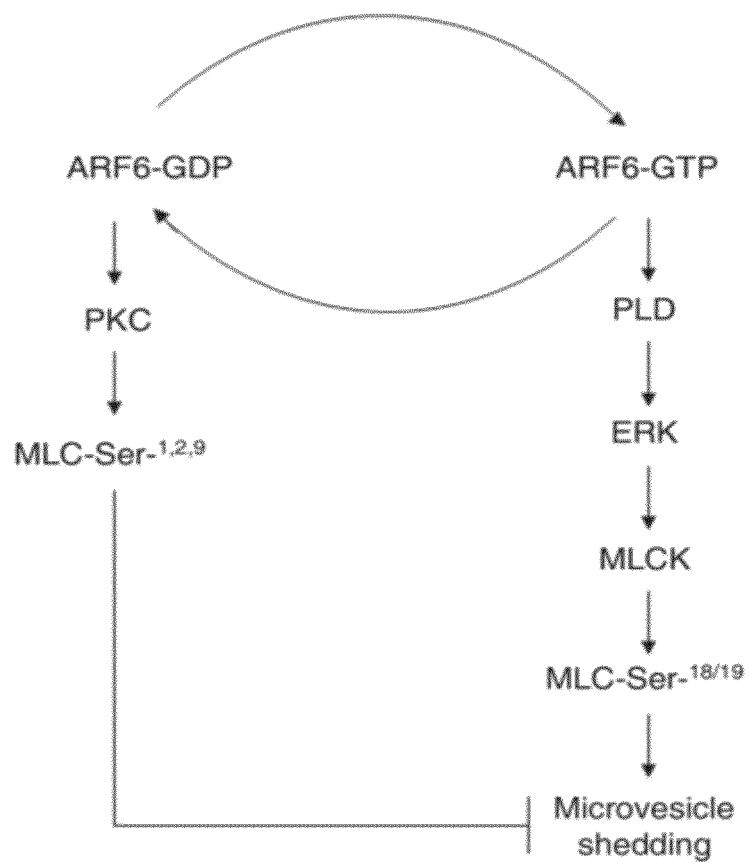
FIG. 7B depicts the signaling pathway downstream of ARF6-regulated ERK activation that is required for microvesicle shedding. ARF6-regulated ERK localization to the plasma membrane, as well as its activation at the plasma membrane, both require PLD. ERK-induced phosphorylation of MLCK, in turn, promotes MLC phosphorylation, which is required for actomyosin-based membrane fission, leading to microvesicle release.

Alternative pathways were also examined, such as the activation of PKC or p38 (P. L. Goldberg et al., *Am. J. Physiol. Lung Cell Mol. Physiol.* 282, L146-54 (2002), N. V. Bogatcheva et al., *Am. J. Physiol. Lung Cell Mol. Physiol.* 285, L415-26 (2003)), for MLC phosphorylation in LOX-ARF6-GDP cells. To distinguish between PKC and p38-mediated phosphorylation of MLC, LOXARF6-GDP cells were treated with SB203580, a p38 inhibitor, or Go6976, a PKC inhibitor. Results showed that phospho-MLC levels were decreased specifically upon PKC inhibition (FIG. 6D). Thus, MLC phosphorylation in LOXARF6-GDP occurs via PKC, and is independent of phospho-ERK. Results also indicated that MLC phosphorylation is independent of PKC in parental LOX and in LOXARF6-GTP cells, as no decrease in phospho-MLC levels was observed in the presence of PKC inhibitor. Thus, in LOXARF6-GDP cells, MLC is phosphorylated by PKC, which is inhibitory, while in LOXARF6-GTP cells, MLC phosphorylation is regulated upstream by ERK, a step that promotes MLC-regulated contraction, and in turn, microvesicle fission (FIG. 7A, FIG. 7B). In sum, ARF6-GTP facilitates microvesicle fission via a mechanism that involves ERK-dependent MLC phosphorylation, and ARF6-GDP has the opposite effect via PKC-induced phosphorylation of MLC.

Example 9

Detection of Invasive Microvesicles in a Biological Sample

In this example, a sample is obtained from a patient suspected of or known to have a tumor. A needle is inserted into the area of the suspected or known tumor and a sample of the ascitic fluid is collected in a syringe. A portion of the fluid is then centrifuged first at about 800 g for about 10 minutes, then at about 2,500 g for about 15 minutes, then at about 10,000 g for 30 minutes. During the centrifugation process, the sample is maintained at a temperature of about 2-8° C. Following the centrifugation process, isolated microvesicles are washed in phosphate buffered saline. Western blot analysis is used to determine the presence or absence of one or more of ARF6, Vamp3, MHC class I, MT1-MMP, β1-integrin and β1-integrin receptor in the microvesicles. The presence of ARF6 protein, and, optionally, one or more of Vamp3, MHC class I, MT1-MMP, β1-integrin and β1-integrin receptor in the isolated microvesicles identifies the population of microvesicles as comprising invasive microvesicles.

What is claimed is:

1. A method of identifying invasive microvesicles in a biological sample, the method comprising the steps of:
   providing a biological sample;
   centrifuging the biological sample to collect a population of microvesicles, and
   assaying the population of microvesicles for the presence of the proteins ARF6 and Vamp3, wherein the presence of ARF6 and Vamp3 identifies the population of microvesicles as comprising invasive microvesicles.

2. The method of claim 1, wherein the biological sample is a biological fluid obtained from a subject.

3. The method of claim 2, wherein the biological fluid comprises one or more of blood, plasma, serum, urine, saliva, or ascites.

4. The method of claim 2, wherein the biological fluid is obtained by washing an anatomical structure of the subject and collecting the wash fluid after it has come in contact with the anatomical structure.

5. The method of claim 1, wherein assaying the prepared population of microvesicles is accomplished by contacting the microvesicles with an antibody that binds to ARF6.

6. The method of claim 1, additionally comprising the step of:
assaying the prepared population of microvesicles for the presence of one or more proteins selected from the group consisting of MHC class I, β1-integrin and β1-integrin receptor.

7. The method of claim 6, wherein the population of microvesicles is assayed by western blot.

8. The method of claim 1, wherein the sample is centrifuged at about 10,000 g.

9. The method of claim 8, wherein the sample is centrifuged at about 2,500 g prior to centrifugation at about 10,000 g.

10. A method of analyzing a population of microvesicles for the presence of invasive microvesicles comprising:
determining whether the protein ARF6 and a processed form of the protein MT1-MMP are present in the population of microvesicles, wherein the presence of ARF6 and the processed form of MT1-MMP indicates that invasive microvesicles are present in the sample.

11. The method of claim 10, additionally comprising determining whether one or more additional proteins selected from the group consisting of Vamp3, MHC class I, β1-integrin and β1-integrin receptor are present in the sample.

12. The method of claim 1, wherein the biological sample is centrifuged at from 5,000 g to 15,000 g.

13. The method of claim 1, additionally comprising assaying the population of microvesicles for the presence of MT1-MMP.

14. The method of claim 12, wherein the sample is centrifuged two or more times at from 5,000 g to 15,000 g.

15. The method of claim 12, additionally comprising centrifuging the sample at from about 1,200 g to about 3,000 g prior to centrifuging the sample at from 5,000 g to 15,000 g.

16. The method of claim 1, wherein the population of microvesicles is assayed for the presence of ARF6 by western blot.

17. The method of claim 1, wherein the biological sample is obtained from a patient suffering from a tumor.

* * * * *

UNITED STATES PATENT AND TRADEMARK OFFICE
CERTIFICATE OF CORRECTION

PATENT NO. : 8,420,334 B2
APPLICATION NO. : 12/942858
DATED : April 16, 2013
INVENTOR(S) : Crislyn D'Souza-Schorey, James W. Clancy and Vandhana Muralidharan-Chari It is certified that error appears in the above-identified patent and that said Letters Patent is hereby corrected as shown below:

In the Specification

At Column 1, Lines 8-10, please delete:
"This invention was made with government support under Grant No. 5R56CA115316-02 awarded by the National Cancer Institute."

And insert:
-- This invention was made with government support under grant CA115316 awarded by the National Institutes of Health. -- therefor.

Signed and Sealed this
First Day of October, 2024

Katherine Kelly Vidal
*Director of the United States Patent and Trademark Office*